US010202523B2

(12) United States Patent
Berry et al.

(10) Patent No.: US 10,202,523 B2
(45) Date of Patent: Feb. 12, 2019

(54) ICE ADHESION REDUCING PREPOLYMERS AND POLYMERS

(71) Applicants: The Boeing Company, Chicago, IL (US); Commonwealth Scientific and Industrial Research Organisation, Acton (AU)

(72) Inventors: Douglas Henry Berry, Seattle, WA (US); Jill Elisabeth Seebergh, Seattle, WA (US); Stuart Arthur Bateman, Melbourne (AU); Ranya Simons, Melbourne (AU); Sheng Li, Melbourne (AU); Lee Russell, Melbourne (AU); Alex Bilyk, Melbourne (AU)

(73) Assignee: THE BOEING COMPANY, Chicago, IL (US)

( * ) Notice: Subject to any disclaimer, the term of this patent is extended or adjusted under 35 U.S.C. 154(b) by 210 days.

(21) Appl. No.: 15/313,820

(22) PCT Filed: May 29, 2015

(86) PCT No.: PCT/AU2015/000323
§ 371 (c)(1),
(2) Date: Nov. 23, 2016

(87) PCT Pub. No.: WO2015/179902
PCT Pub. Date: Dec. 3, 2015

(65) Prior Publication Data
US 2017/0204291 A1 Jul. 20, 2017

Related U.S. Application Data

(60) Provisional application No. 62/005,637, filed on May 30, 2014.

(51) Int. Cl.
| C08G 77/24 | (2006.01) |
| C09D 183/10 | (2006.01) |
| B05D 5/00 | (2006.01) |
| C07F 7/21 | (2006.01) |
| C08G 18/61 | (2006.01) |
| C09D 175/04 | (2006.01) |
| C08G 77/04 | (2006.01) |
| C08G 77/388 | (2006.01) |
| C08G 77/42 | (2006.01) |
| C09D 5/00 | (2006.01) |
| C08G 18/73 | (2006.01) |
| C08G 77/458 | (2006.01) |

(52) U.S. Cl.
CPC ............ *C09D 183/10* (2013.01); *B05D 5/00* (2013.01); *C07F 7/21* (2013.01); *C08G 18/61* (2013.01); *C08G 18/73* (2013.01); *C08G 77/045* (2013.01); *C08G 77/24* (2013.01); *C08G 77/388* (2013.01); *C08G 77/42* (2013.01); *C08G 77/458* (2013.01); *C09D 5/00* (2013.01); *C09D 175/04* (2013.01)

(58) Field of Classification Search
CPC ........ C08G 77/24; C08G 77/26; C08G 77/14; C08G 77/458; C08G 18/61; C07F 7/21
USPC .................................................... 528/28, 38
See application file for complete search history.

(56) References Cited

U.S. PATENT DOCUMENTS

| 6,797,795 B2 | 9/2004 | Byrd |
| 6,809,169 B2 | 10/2004 | Byrd et al. |
| 7,122,599 B2 | 10/2006 | Haubennestel et al. |
| 7,897,667 B2 * | 3/2011 | Mabry .................. B82Y 30/00 524/269 |
| 7,910,683 B2 | 3/2011 | Byrd et al. |
| 8,748,501 B2 * | 6/2014 | Hwang .............. C08G 18/4825 521/110 |
| 2003/0235696 A1 | 12/2003 | Byrd |
| 2005/0033077 A1 | 2/2005 | Yamahiro et al. |
| 2006/0167206 A1 | 7/2006 | Maier et al. |
| 2008/0096027 A1 | 4/2008 | Byrd et al. |
| 2009/0263664 A1 | 10/2009 | Byrd et al. |
| 2014/0088219 A1 | 3/2014 | Chen et al. |
| 2015/0065674 A1 * | 3/2015 | Ramirez .............. C08G 77/045 528/26 |

(Continued)

FOREIGN PATENT DOCUMENTS

| CN | 102757708 A | 10/2012 |
| CN | 1003468120 A | 12/2013 |
| EP | 1193303 A2 | 4/2002 |

OTHER PUBLICATIONS

Zhu et al., "Ice-Phobic Coatings Based on Silicon-Oil_Infused Polydimethysiloxane," ACS Appl. Mater. Interfaces 2013, 5, 4053-4062.
First Examination Report dated Jul. 27, 2018 corresponding to Australian Application No. 2015268085.
Kannan et al., "Fluoro-silsesquioxane-urethane hybrid for thin film applications," Applied Materials and Interfaces, vol. 1, No. 2, 2009, pp. 336-347.
Office Action dated Jul. 10, 2018 in corresponding Chinese Application No. 201580041807.2.

(Continued)

Primary Examiner — Margaret G Moore
(74) Attorney, Agent, or Firm — MH2 Technology Law Group LLP

(57) ABSTRACT

The present disclosure relates to an FPOSS prepolymer which may be reacted with a reactive coating or a polyisocyanate and/or one or more of a polysiloxane, a polyol, a polyamine and a reactive coating; an FPOSS polyisocyanate prepolymer which may be reacted with one or more of a polysiloxane, a polyol, a polyamine or a reactive coating; and an FPOSS siloxane prepolymer which may be reacted with a polyisocyanate and/or one or more of a polyol, a polyamine or a reactive coating to form cross-linked polymers capable of reducing the ability of ice to adhere to the surface of an object, in particular aircraft or other vehicles, methods of producing the prepolymers and polymers and their use in coating surfaces.

20 Claims, 3 Drawing Sheets

(56) References Cited

U.S. PATENT DOCUMENTS

| | | |
|---|---|---|
| 2015/0152270 A1 | 6/2015 | Aizenberg et al. |
| 2016/0009971 A1 | 1/2016 | Wang et al. |
| 2016/0083612 A1* | 3/2016 | Catchings, Sr. ..... C09D 133/16 |
| | | 526/266 |
| 2017/0218209 A1* | 8/2017 | Yuan ........................ C09K 3/18 |
| 2017/0275437 A1* | 9/2017 | Diao ..................... C08K 5/549 |

OTHER PUBLICATIONS

Examination Report No. 1 dated May 18, 2018 for corresponding Australian Patent Application No. 2015268086, 3 pages.

Kannan et al., "Fluoro-silsesquioxane-urethane hybrid for thin film applications," ACS Applied Materials & Interfaces, vol. 1, No. 2, Feb. 25, 2009, pp. 336-347.

Extended Eureopean Search Report from related European Patent Application No. 15800372.3, dated Dec. 22, 2017.

Extended Eureopean Search Report from related European Patent Application No. 15799288.4, dated Jan. 24, 2018.

\* cited by examiner

ICE ADHESION REDUCING PREPOLYMERS AND POLYMERS

FIELD

The present disclosure relates to prepolymers and polymers capable of mitigating the effects of ice build-up on surfaces by reducing the ability of ice to adhere to the surface of an object, in particular aircraft or other vehicles, methods of producing the prepolymers and polymers and their use in coating surfaces.

BACKGROUND

The everyday build-up of ice upon the surfaces of objects is a familiar annoyance and often a safety hazard. The layers of ice that form on highways, driveways, and walkways make transportation difficult. The masses of ice that accumulate within or upon industrial, agricultural, or other mechanical equipment make operation of the equipment difficult or impossible. The weight of ice on power lines, buildings, wind turbines, refrigeration units, air conditioning and signs often impairs those structures.

Build-up of ice upon the wings and components of an aircraft is of particular concern. The lift generated by the wings, and thus the ability of the aircraft to become and remain airborne, is dependent on the shape of the wings. Even a small accumulation of ice upon the surface of the wings can significantly increase drag and dramatically reduce lift. Further, ice build-up along control surfaces of the aircraft can impede the movement of those surfaces.

There are a large variety of techniques used to control the build-up of ice upon the wings and other surfaces of aircraft. For instance, the aircraft may be deiced before take-off by radiant heat energy or by application of a chemical spray which melts the ice from the wings. Such deicing sprays are not an environmentally preferred solution. The ritual of deicing is well known to airline passengers traveling through cold environments.

Another method of deicing aircraft on the ground or in the air includes providing flexible pneumatic coverings (bladders) along the leading edges of the wings, and supplying bursts of air or fluid to expand the flexible coverings to break away any overlying ice. Similarly, bleeding air from the aircraft engine and routing the heated air to the surface of the wing heats the wing and melts the ice. Ice may also be removed from the wing by providing mechanical energy to the wing, such as through the use of electrically actuated thumpers, which causes the wing to vibrate, fracturing any accumulated ice or by the use of electric blankets.

Although the previously mentioned methods of ice removal are generally effective, they require the continuous supply of air, chemicals, or electrical power in order to rid the wing of its burden. It would be preferred, of course, to reduce the adhesion of ice in the first place.

One might expect that known non-stick coatings would be able to reduce ice from adhering to the surfaces which they coat. It has been found that aluminium surfaces coated with a polytetrafluoroethylene material do show a reduction in adhesion (aluminium 1576 kPa, Teflon 238 kPa), but not as much as might be expected. Further, upon repeated freezing, the favourable properties exhibited by polytetrafluoroethylene and similar coatings can degrade, resulting in a coating with little or no anti-icing capacity.

There is a need for a method which provides a durable surface with low ice adhesion properties and/or delayed freezing, which eliminates or at least reduces the continuous supply of air, chemicals or electrical power in order to reduce the amount of ice forming on a surface and/or the adhesion of ice to the surface.

SUMMARY

There is provided an FPOSS prepolymer which may be reacted with a reactive coating or a polyisocyanate and optionally one or more of a polysiloxane, a polyol, a polyamine and a reactive coating; an FPOSS polyisocyanate prepolymer which may be reacted with one or more of a polysiloxane, a polyol, a polyamine or a reactive coating; and an FPOSS siloxane prepolymer which may be reacted with a polyisocyanate and/or one or more of a polyol, a polyamine or a reactive coating to form an at least partially cross-linked polymer which is capable of reducing the adherence of ice to a surface or reducing the build-up of ice on a surface. There is also provided methods of producing the prepolymers and polymer and a method of coating objects such as vehicles, particularly aircraft, with the polymer. The polymer forms an ice reducing polymer coating when employed upon a surface of an object. Alternatively, the polymer may be used as a component of an existing coating to provide ice reducing properties to the coating. When coated upon a surface, it is believed that the polymer disrupts bonding between ice and the polymer coated surface. Moreover, if ice does form, it is believed that the polymer disrupts the hydrogen bonding between the ice and the polymer coated surface, thereby diminishing the ability of the ice to adhere to the polymer surface. The ability of the polymer coating to adhere to surfaces and to reduce the formation of ice upon polymer coated surfaces, makes the polymer particularly useful for reducing the adherence of ice to surfaces or reducing the build-up of ice on surfaces of objects such as power lines, buildings, wind turbines, refrigeration units and aircraft or other vehicles.

In a first aspect, there is provided an FPOSS prepolymer of the formula (I):

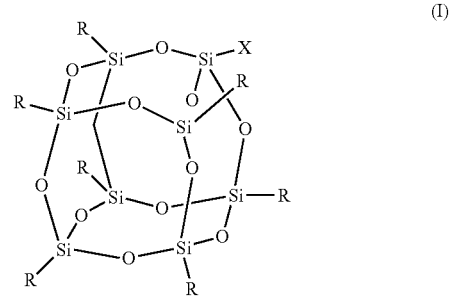

(I)

in which X is a branched or unbranched side chain of 1 to 20 carbons comprising one or more functional groups selected from amino, hydroxy, epoxy, isocyanate, thiol, anhydride, ether, ester or ketone, wherein the functional groups are either present as end groups, or on one or more C atoms of the side chain;

R is independently selected from the group consisting of a polyisocyanate and optionally substituted $C_{1-20}$ alkyl which may be optionally interrupted with O, C=O, N=C=O, CH(OH), $CH_2OR^{11}$, $CH_2SR^{11}$ and $(CH_2)_m(CF_2)_n CF_3$ provided that at least one R is $(CH_2)_m(CF_2)_n CF_3$;

m is 1 to 20;

n is 0 to 20; and $R^{11}$ is H or optionally substituted $C_{1-16}$ alkyl.

Preferably X is (CH$_2$)$_2$OC(O)NH(CH$_2$)$_2$OC(O)CH (NCO) (CH$_2$)$_4$NCO (lysine triisocyanate FPOSS), (CH$_2$)$_n$OH, (CH$_2$)$_n$NH$_2$, (CH$_2$)CO$_2$CH$_3$, (CH$_2$)$_n$CO$_2$N((CH$_2$)$_2$OH)$_2$, (CH$_2$)$_n$OCH$_2$CH(OH)CH$_2$OH, or optionally substituted C$_{1-20}$ alkyl which may be optionally interrupted by O, CH$_2$O, Si, NH, NR$^{11}$, C═O, CH(OH), NH, CR(NCO), (CH$_2$)$_n$ or CO$_2$.

The FPOSS prepolymer can be used as an additive for an existing coating formulation (FIG. 1A) or used as an additive with polysiloxane/polyisocyanate based coating formulations (FIG. 1B). Alternatively, the FPOSS prepolymer can be linked to a polyisocyanate (FIG. 1C).

In a second aspect, there is provided an FPOSS polyisocyanate prepolymer of the formula (I) defined above in which X is (CH$_2$)$_n$OL, (CH$_2$)$_n$NHL or optionally substituted (CH$_2$)$_m$L which may be optionally interrupted with O, CH$_2$O, Si, NH, NR$^{11}$, C═O, CH(OH), NH, CR(NCO), (CH$_2$)$_n$ or CO$_2$ in which L denotes the position at which a polyisocyanate is attached and R, m, n and R$^{11}$ are as defined in formula (I) above.

The FPOSS polyisocyanate prepolymer can form part of the isocyanate backbone of polymers and coatings. This embodiment is shown in FIG. 1D.

The FPOSS prepolymer can also be linked to one or more polysiloxanes to form an FPOSS siloxane prepolymer. This embodiment is shown in FIGS. 2 and 3.

In a third aspect, there is provided an FPOSS siloxane prepolymer of the formula (II):

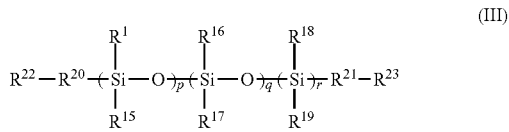

(II)

in which

R$^1$ to R$^6$ are independently selected from the group consisting of H; optionally substituted C$_{1-16}$ alkyl optionally interrupted with a group selected from NR$^{11}$, C═O, C═C, S, CO$_2$, O and CH(NCO); OSiR$^{12}$$_3$; (CH$_2$)$_n$OH; (CH$_2$)$_n$O(CH$_2$)$_n$OH; (CH$_2$)$_n$ NR$^{11}$R$^{12}$; (CH$_2$)$_n$NH(CH$_2$)$_n$ NR$^{11}$R$^{12}$; (CH$_2$)$_n$O(CH$_2$)$_n$ NR$^{11}$R$^{12}$; (CH$_2$)$_n$NCO; epoxy; (CH$_2$)$_n$F-POSS of formula (I), optionally substituted C$_{1-16}$ alkylaryl; optionally substituted aryl; optionally substituted polyaryl; optionally substituted C$_{3-6}$cycloaliphatic; and optionally substituted C$_{3-6}$ heterocyclyl;

R$^7$ and R$^8$ are independently absent or independently selected from the group consisting of optionally substituted C$_{1-16}$ alkyl optionally interrupted with a group selected from NR$^{11}$, C═O, C═C, S, CO$_2$, O and CH(NCO); O; S; OSi(R$^{13}$)$_2$; (CH$_2$)$_n$; (CH$_2$)$_n$NH; (CH$_2$)$_n$O; optionally substituted C$_{1-16}$ alkylaryl; optionally substituted aryl; optionally substituted polyaryl; optionally substituted C$_{3-6}$cycloaliphatic; and optionally substituted C$_{3-6}$ heterocyclyl;

R$^9$ and R$^{10}$ are independently selected from the group consisting of H, OH, NR$^{11}$R$^{12}$, optionally substituted C$_{1-16}$ alkyl, NCO, epoxy, Si(R$^{13}$)$_3$ and FPOSS of formula (I);

R$^{11}$ and R$^{12}$ are independently selected from the group consisting of H and optionally substituted C$_{1-16}$ alkyl;

R$^{13}$ is selected from the group consisting of optionally substituted C$_{1-16}$ alkyl, (CH$_2$)$_n$OH and (CH$_2$)$_n$NH$_2$;

n is 1 to 16;

x and z are independently selected from 1 to 1500; and y is 0 to 1500, with the proviso that at least one of R$^1$ to R$^6$, R$^9$ and R$^{10}$ is the FPOSS prepolymer of the formula (I) defined above in which X is (CH$_2$)$_2$OC(O)NH(CH$_2$)$_2$OC(O)CH (NHCOY) (CH$_2$)$_4$ NHCOY' (lysine triisocyanate linked siloxane), (CH$_2$)$_n$OY, (CH$_2$)$_n$NHY or optionally substituted (CH$_2$)$_m$Y which may be optionally interrupted with O, CH$_2$O, Si, NH, NR$^{11}$, C═O, CH(OH), NH, CR(NCO), (CH$_2$)$_n$ or CO$_2$;

Y and Y' denote positions at which the FPOSS prepolymer of formula (I) can be linked to the FPOSS siloxane prepolymer of formula (II) and R, m, n and R$^{11}$ are as defined in formula (I) above.

In a fourth aspect, there is provided a polymer comprising a cross-linked reaction product of the following:
(i) the FPOSS prepolymer of the formula (I) defined above and a reactive coating [FIG. 1A];
(ii) the FPOSS prepolymer of the formula (I) defined above, a polyisocyanate and one or more of a polysiloxane of formula (III) [FIG. 1B]:

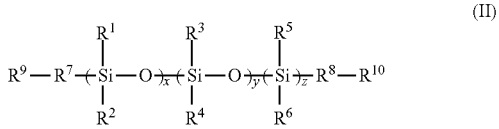

(III)

in which

R$^{14}$ to R$^{19}$ are independently selected from the group consisting of hydrogen; optionally substituted C$_{1-16}$ alkyl optionally interrupted with a group selected from NR$^{24}$, C═O, C═C, S, CO$_2$, O and CH(NCO); OSiR$^{25}$$_3$; (CH$_2$)$_n$OH; (CH$_2$)$_n$O(CH$_2$)OH; (CH$_2$)$_n$ NR$^{24}$R$^{25}$; (CH$_2$)NH(CH$_2$)$_n$ NR$^{24}$R$^{25}$; (CH$_2$)$_n$O(CH$_2$)$_n$ NR$^{24}$R$^{25}$; (CH$_2$)$_n$NCO; epoxy; optionally substituted C$_{1-16}$ alkylaryl; optionally substituted aryl; optionally substituted polyaryl; optionally substituted C$_{3-6}$ cycloaliphatic; and optionally substituted C$_{3-6}$ heterocyclyl;

R$^{20}$ and R$^{21}$ are independently absent or independently selected from the group consisting of optionally substituted C$_{1-16}$ alkyl optionally interrupted with a group selected from NR$^{24}$, C═O, C═C, S, CO$_2$, O and CH(NCO); O; S; OSi(R$^{26}$)$_2$; (CH$_2$)$_n$; (CH$_2$)$_n$NH; (CH$_2$)$_n$O; optionally substituted C$_{1-16}$ alkylaryl; optionally substituted aryl; optionally substituted polyaryl; optionally substituted C$_{3-6}$ cycloaliphatic; and optionally substituted C$_{3-6}$ heterocyclyl;

R$^{22}$ and R$^{23}$ are independently selected from the group consisting of H, OH, NR$^{11}$R$^{12}$, optionally substituted C$_{1-16}$ alkyl, NCO, epoxy and Si(R$^{13}$)$_3$;

R$^{24}$ and R$^{25}$ are independently selected from the group consisting of H and optionally substituted C$_{1-16}$ alkyl;

R$^{26}$ is selected from the group consisting of optionally substituted C$_{1-16}$ alkyl, (CH$_2$)$_n$OH and (CH$_2$)$_n$NH$_2$;

n is 1 to 16;

p and r are independently selected from 1 to 1500; and q is 0 to 1500, a polyol, a polyamine and a reactive coating;
(iii) the FPOSS polyisocyanate prepolymer defined above, one or more of the polysiloxane of formula (III) defined above and optionally a polyol, a polyamine or a reactive coating [FIG. 1C];
(iv) a 1:2-14:15 ratio of the FPOSS polyisocyanate prepolymer defined above and a siloxane of the formula (III) defined above [FIG. 1D];

(v) the FPOSS siloxane prepolymer of the formula (II) defined above and a polyisocyanate and optionally one or more of a polyol, a polyamine or a reactive coating [FIGS. 2 and 3], with the provisos that:

(a) when the siloxane of formula (II) or (III) reacts with a polyisocyanate, then at least one of $R^1$ to $R^6$, $R^9$ and $R^{10}$ or $R^{14}$ to $R^{18}$ and $R^{22}$ and $R^{23}$ must bear at least one OH or $NH_2$ or both;

(b) when the siloxane of formula (II) or (III) reacts with a polyol, a polyamine or a reactive coating, then at least one of $R^1$ to $R^6$, $R^9$ and $R^{10}$ or $R^{14}$ to $R^{18}$ and $R^{22}$ and $R^{23}$ must bear at least one NCO; and (c) when the siloxane of formula (II) or (III) reacts with a reactive coating, then at least one of $R^1$ to $R^6$, $R^9$ and $R^{10}$ or $R^{14}$ to $R^{18}$ and $R^{22}$ and $R^{23}$ must bear at least one OH or $NH_2$ or both to react with a polyisocyanate present in the reactive coating or at least one of $R^1$ to $R^6$, $R^9$ and $R^{10}$ must bear at least one NCO to react with a polyol or polyamine present in the coating.

The polymer is an ice reducing polymer which means that the polymer is capable of reducing the adherence of ice to a surface or reducing the build-up of ice on a surface and does not imply the total prevention of ice accretion on a surface.

In a fifth aspect, there is provided an ice reducing polymer comprising the polymer defined above.

In a sixth aspect, there is provided a polymer formulation comprising the polymer defined above, a solvent and an optional additive such as an extender, catalyst and/or cross-linking agent.

The polymer or polymer formulation may be in the form of a polymer coating or can be present as an additive to an existing coating. The polymer and the polymer coating are cross-linked. The cross-linking can be within the ice reducing polymer coating layer as well as between the polymer coating and adjacent existing coatings.

In a sixth aspect, there is provided a method of producing the prepolymer and polymer defined above as described herein.

In a seventh aspect, there is provided an object comprising an external surface in which at least a portion of the external surface is coated with the polymer or polymer formulation defined above.

In an eighth aspect, there is provided a method of imparting ice reducing properties to at least a portion of an external surface of an object comprising applying a coating of the polymer or polymer formulation defined above onto the surface.

In a ninth aspect, there is provided an object comprising components with surfaces coated with the polymer or polymer formulation defined above.

BRIEF DESCRIPTION OF THE DRAWINGS

The accompanying drawings, which are incorporated in and constitute a part of this specification, illustrate the present disclosure and together with the description, serve to explain the principles of the present disclosure.

DETAILED DESCRIPTION

Figure 1:
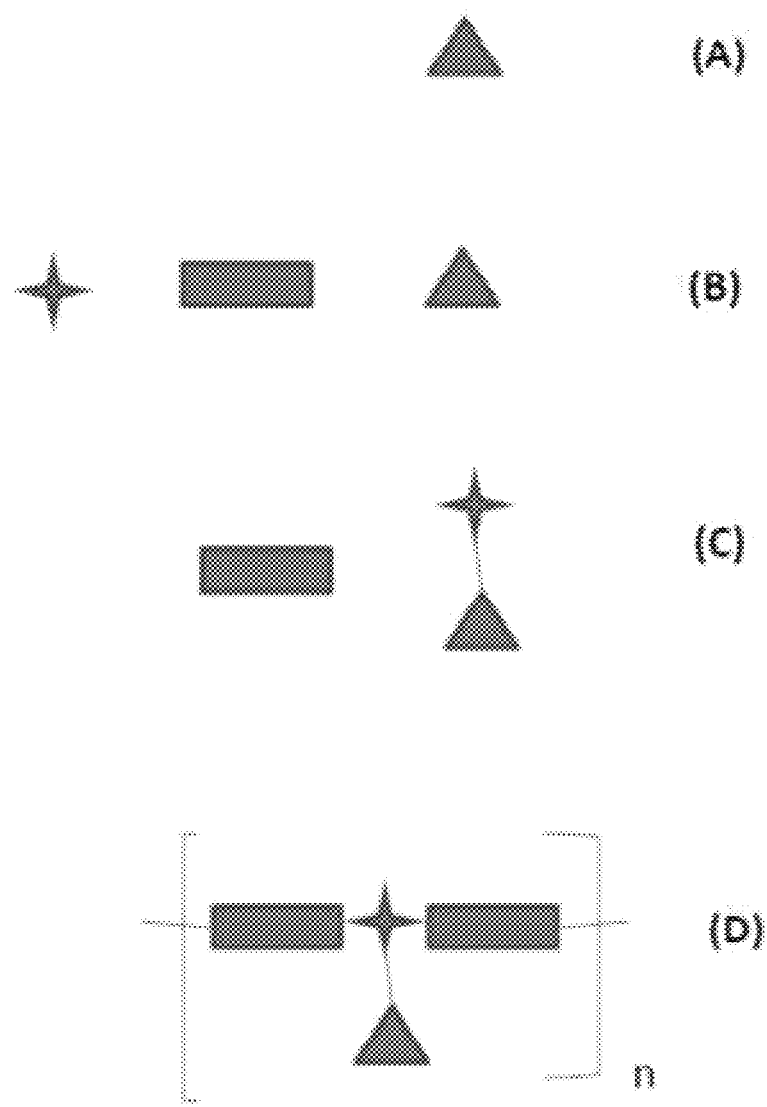
FIG. 1A schematically depicts a fluorinated polyhedral oligomeric silsequioxane (FPOSS) prepolymer used as an additive for an existing coating formulation according to the present disclosure.
FIG. 1B schematically depicts a FPOSS compound used as an additive with polysiloxane/polyisocyanate based coating formulations according to the present disclosure.
FIG. 1C schematically depicts a FPOSS prepolymer linked to a polyisocyanate according to the present disclosure.
FIG. 1D schematically a FPOSS polyisocyanate prepolymer forming part of the isocyanate backbone of polymers and coatings according to the present disclosure.
Figure 2:
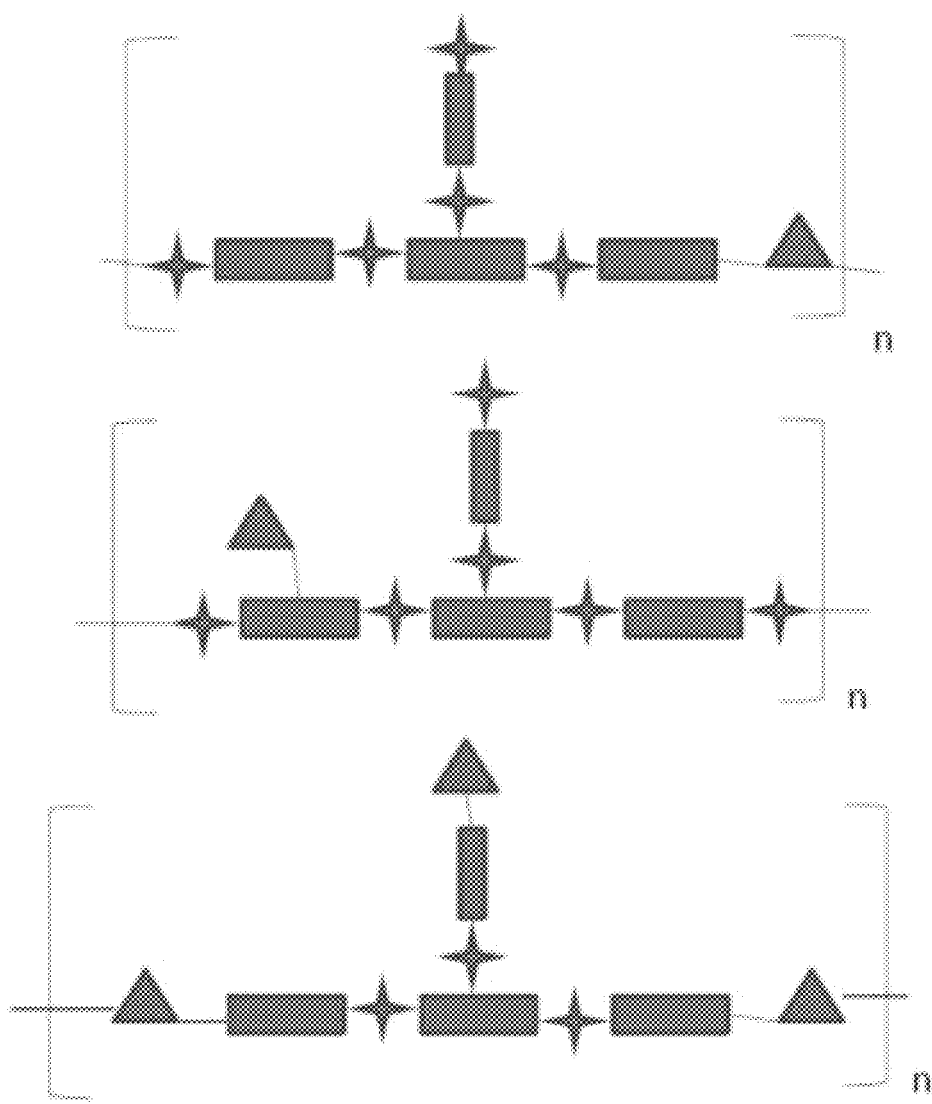
FIG. 2 schematically depicts a FPOSS prepolymer linked to one or more polysiloxanes to form a FPOSS siloxane prepolymer according to the present disclosure.

The disclosure relates to the prepolymers, polymers and polymer formulations as defined above which provides an improved polymer coating which reduces the ability of ice to adhere and/or form upon a coated surface. The polymer coating is particularly effective when applied to a surface of an object. For example, coated or uncoated metal, including aerospace alloys of aluminium, stainless steel, or titanium or to coated or uncoated resin composites having glass, ceramic, or carbon fiber reinforcement and is particularly useful for reducing the formation of ice upon the control or aerodynamic lifting surfaces of aircraft or space vehicles. The polymer coating also forms an effective ice reducer when used on a wide variety of materials other than the preferred aluminium, titanium or carbon composite, such as glass and polymeric materials.

In use the polymer formulation could be applied to the surface, especially to an aircraft, to retain its functionality under a variety of environmental conditions, such as those typically encountered by commercial or military aircraft. A method of applying the polymer formulation to at least a portion of the surface of an object, such as an aircraft, is also provided.

Definitions

The alkyls may be linear or branched, saturated or unsaturated, substituted or unsubstituted and contain 1 to 16 carbon atoms.

Examples of saturated alkyls include methyl, ethyl, propyl, isopropyl, butyl, isobutyl, sec-butyl, tert-butyl, pentyl, neopentyl, hexyl and the like.

Examples of unsaturated alkyls include alkenyls such as vinyl, 1-propenyl, 1-and 2-butenyl, 2-methyl-2-propenyl and the like or alkynyls such as ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl and the like.

Unless the context requires otherwise, the term "alkyl" also encompasses alkyl groups containing one less hydrogen atom such that the group is attached via two positions i.e. divalent.

The aryls may be $C_6$, $C_{10}$, $C_{14}$ aryls selected from phenyl, naphthyl and tetrahydronapthyl.

The alkylaryls may be linear or branched, saturated or unsaturated, substituted or unsubstituted such as benzyl.

The polyaryls are two or more aryls linked by at least one carbon-carbon bond and may be selected from biphenyl and terphenyl. The polyaryls may be linear or branched, substituted or unsubstituted.

The $C_{3-6}$ cycloaliphatic is a non-aromatic cyclic group having from 3 to 6 carbon atoms and includes $C_{3-6}$ cycloalkyls such as cyclopropyl, cyclobutyl, cyclopentyl and cyclohexyl. It will be understood that cycloalkyl groups may be saturated such as cyclohexyl or unsaturated such as cyclohexenyl.

The $C_{3-6}$ heterocyclyls may be saturated or unsaturated, substituted or unsubstituted and include saturated or unsaturated 3-6 membered rings having heteroatoms selected from O, N and S.

The term "optionally substituted" refers to a group which may or may not be further substituted with 1, 2, 3, 4 or more groups, preferably 1, 2 or 3, more preferably 1 or 2 groups selected from the group consisting of $C_{1-6}$ alkyl, $C_{2-6}$ alkenyl, $C_{2-6}$ alkynyl, $C_{3-8}$ cycloalkyl, hydroxyl, oxo, $C_{1-6}$ alkoxy, aryloxy, $C_{1-6}$ alkoxyaryl, halo, $C_{1-6}$ alkylhalo (such as $CF_3$ and $CHF_2$), $C_{1-6}$ alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, isocyanates, sulfates, sulfonates, sulfinyl, substituted sulfinyl, sulfonyl, substituted sulfonyl, sulfonylamides, substituted sulfonamides, disubstituted sulfonamides, aryl, $C_{1-6}$ alkyl, heterocyclyl and heteroaryl wherein each alkyl, alkenyl, alkynyl, cycloalkyl, aryl and heterocyclyl and groups containing them may be further optionally substituted. In one example, the optional substituents are selected from the group consisting of $C_{1-6}$ alkyl, hydroxyl, amino, substituted amino, disubstituted amino, isocyanate and $C_{1-6}$ alkoxy.

Formula (I)

The compound of formula (I) is also known as FPOSS (fluorinated polyhedral oligomeric silsequioxanes). It demonstrates both oleophobic and hydrophobic behaviour from its fluorinated side chains along with the capacity to impart nano-scale morphological features on a surface via its cage structure.

A variety of FPOSS compounds have been prepared, the synthesis methodology optimized, and the compounds purified and characterized for use as modifiers. The FPOSS derivatives include (i) tri-fluoropropyl POSS (TFP-POSS) (ii) tri-decafluoro(octyl)POSS (TDF(Octyl)POSS) and (iii) hydroxyl functional tri-fluoropropyl POSS (Hydroxy TFP POSS), Scheme 1 and 2.

Scheme 1 Synthesis of Tri-fluoropropyl POSS

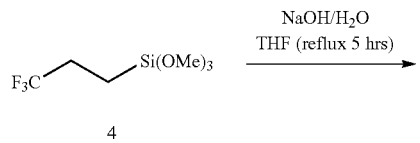

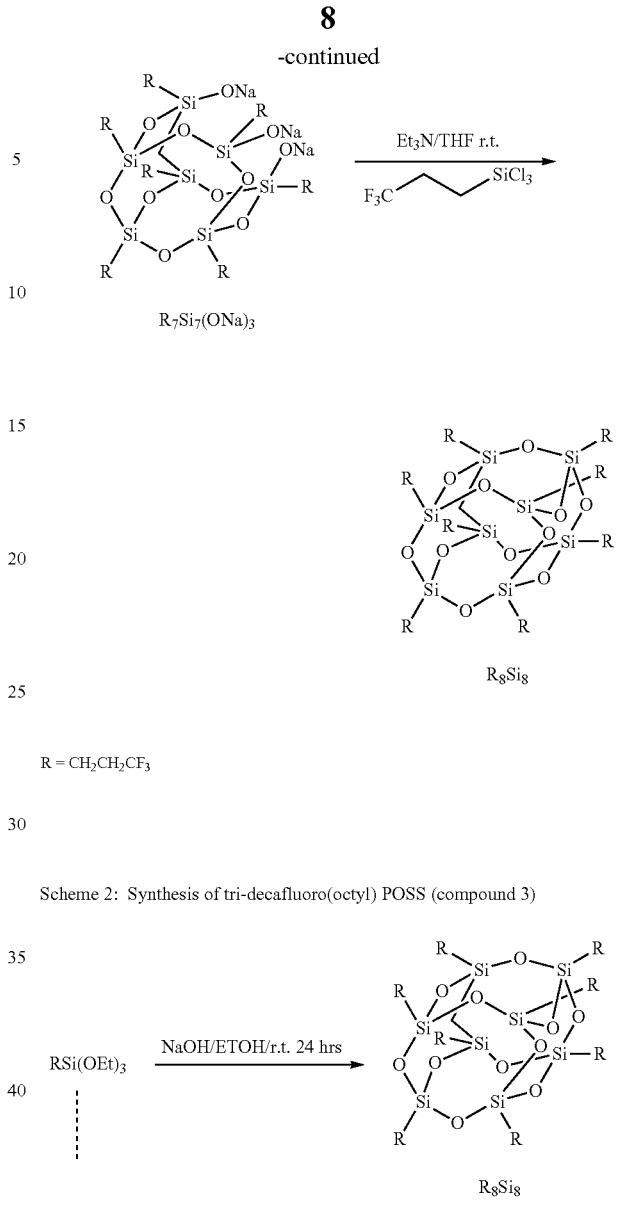

Scheme 2: Synthesis of tri-decafluoro(octyl) POSS (compound 3)

2, 3 or 4 where
2. R = $CH_2CH_2CF_2CF_2CF_2CF_3$ (nonaflurohexyl)
3. R = $CH_2CH_2CF_2CF_2CF_2CF_2CF_2CF_3$ (tridecaflurooctyl)
4. R = $CH_2CH_2CF_2CF_2CF_2CF_2CF_2CF_2CF_2CF_3$ (heptadecafluorodecyl)

Scheme 3: Synthesis of (mono) hydroxyl funtional trifluoropropyl POSS

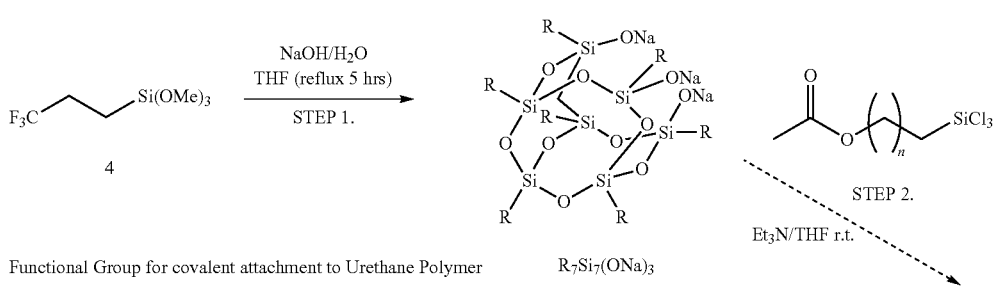

Functional Group for covalent attachment to Urethane Polymer

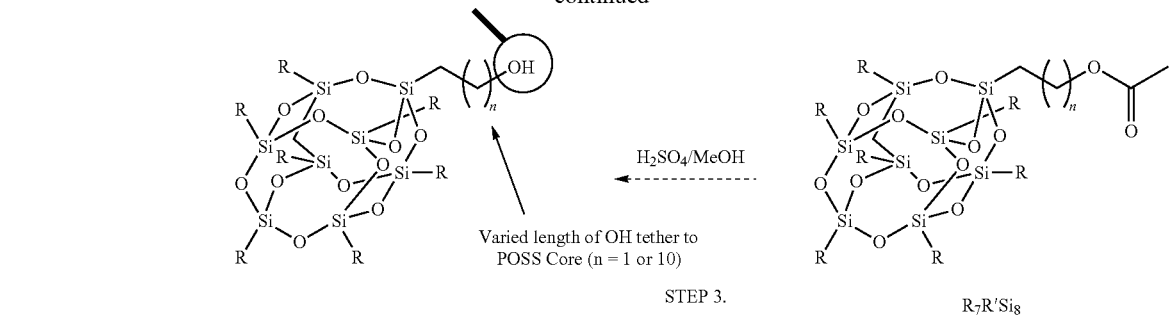

STEP 3.

R = —CH₂CH₂CF₃

R' = alcohol functionalised arm

An alternate route is to synthesise diisocyanate functional FPOSS as described above which can then be reacted with the polyol component of a polyurethane coating such as the Desothane® HS CA8000 series. Initial synthesis of these compounds (Scheme 4) has been successful, and Fourier transform infrared spectroscopy (FTIR) indicates that the diisocyanate group is available for further reaction with the polyol component of the coating.

Scheme 3: Synthesis of diisocyanate functional FPOSS

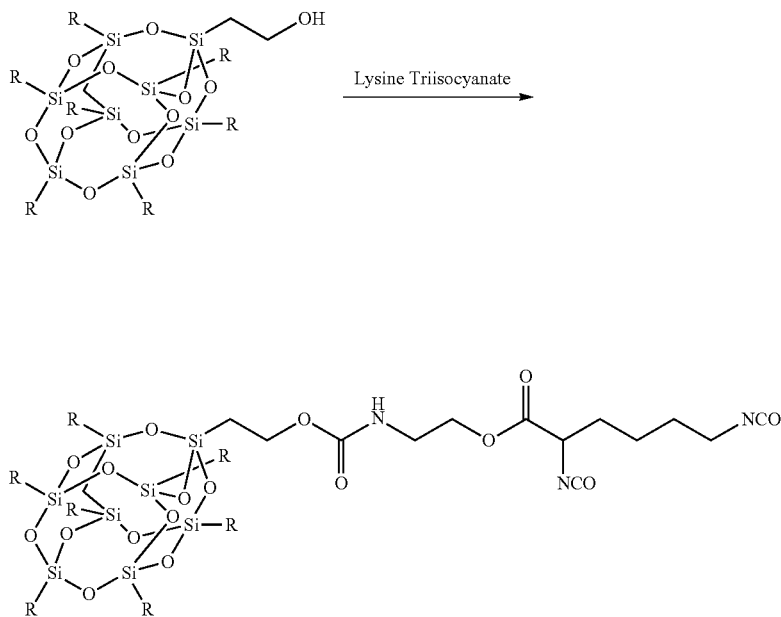

Formula (II) and (III)

The compound of formula (II) is an FPOSS siloxane prepolymer when at least one of $R^1$ to $R^6$, $R^9$ and $R^{10}$ is FPOSS.

In one example, the FPOSS siloxane prepolymer is the reaction product of about 15:14 to 2:1 polysiloxane (III): FPOSS polyisocyanate prepolymer. The resulting FPOSS siloxane prepolymer in turn can be reacted with a further polyisocyanate, polyol and/or polyamine. The further polyisocyanate, polyol and/or polyamine can be any polyisocyanate, polyol or polyamine described in herein or found in reactive coatings such as polyurethane coatings, for example, the Desothane® HS CA8000 series.

Alternatively, the FPOSS siloxane prepolymer can be used as an additive of up to 99% in an ice reducing polymer described in the applicant's co-pending application filed concurrently.

Figure 3:
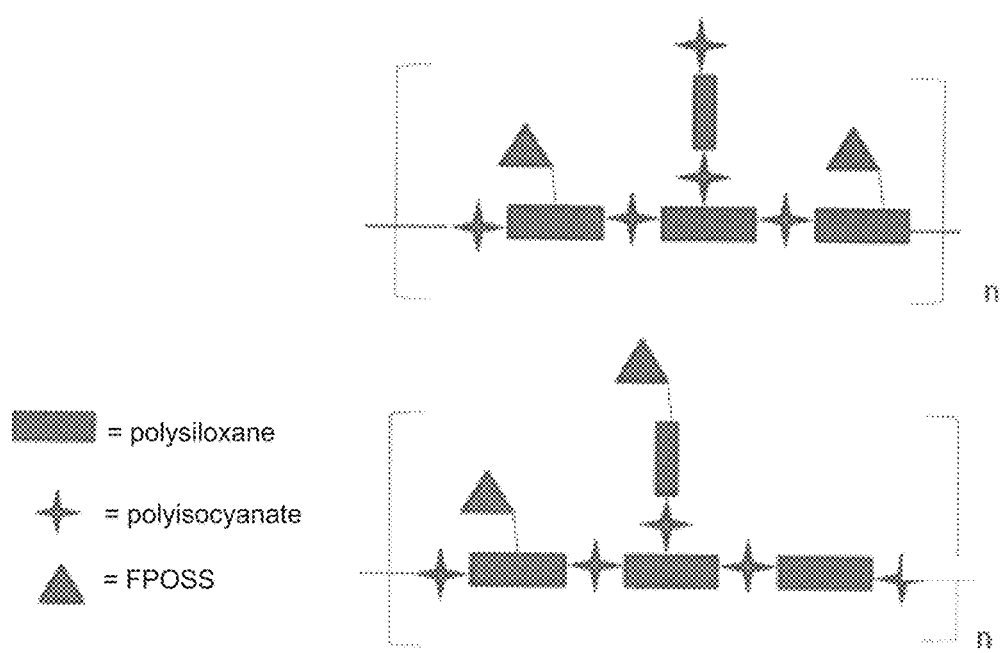
FIG. 3 schematically depicts a FPOSS prepolymer linked to one or more polysiloxanes to form a FPOSS siloxane prepolymer according to the present disclosure.
Figure 3:
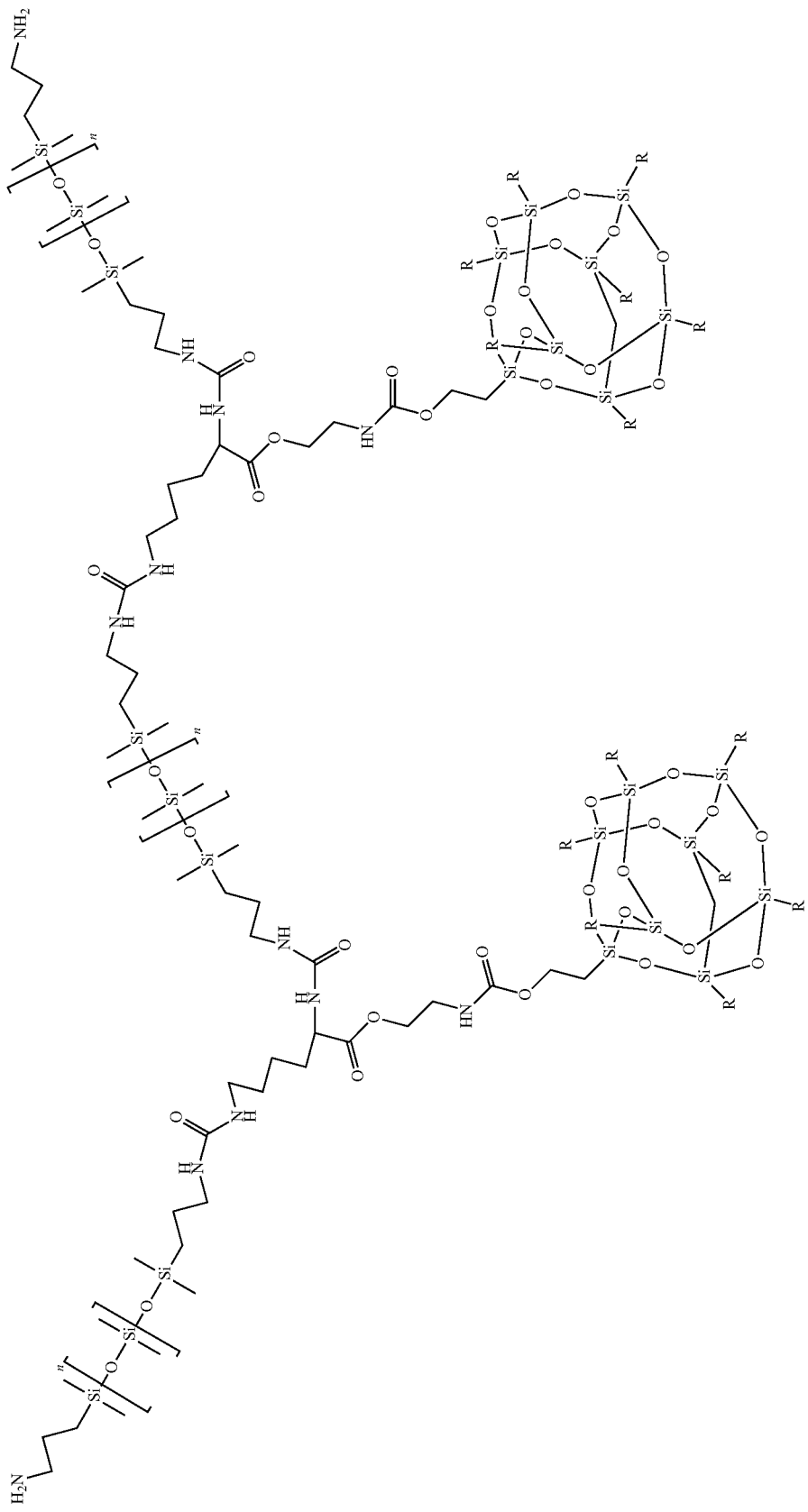

A representative example of a FPOSS siloxane prepolymer is a reaction product of the following:
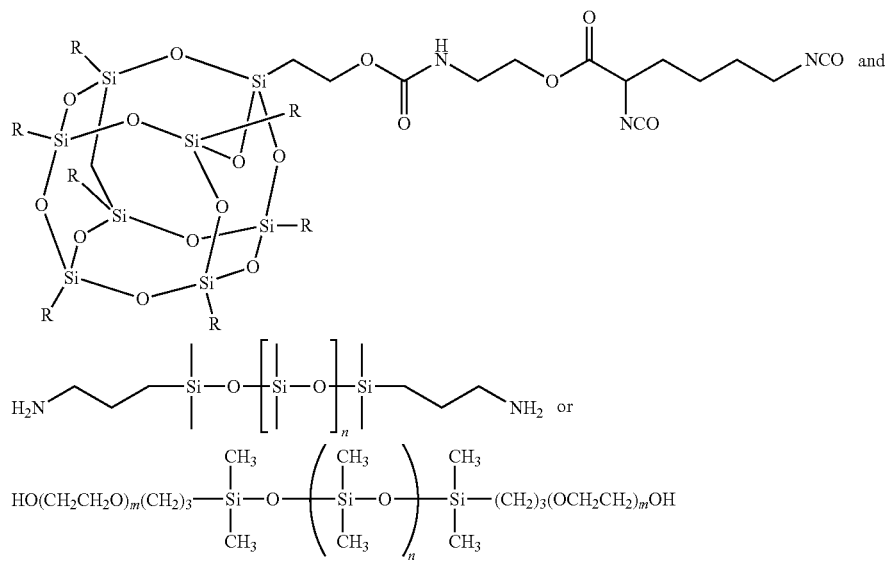
to afford FIG. 3.

Any reactive FPOSS siloxane prepolymers made using siloxanes of formula (II) or (III) may be used provided they are capable of reacting with polyisocyanate and/or a polyol, a polyamine or a reactive coating. Examples of reactive siloxanes include amino functional siloxanes, carbinol functional siloxanes, isocyanate functional siloxanes and epoxy functional siloxanes. Such siloxanes also contain at least one FPOSS as in formula (II). Alternatively, the siloxanes of formula (III) can be reacted with a source of FPOSS such as the polyisocyanate functional FPOSS shown above.

The compound of formula (II) is an amino functional siloxane when the terminal group on any one of $R^1$ to $R^6$, $R^9$ and $R^{10}$ is $NH_2$, a carbinol functional siloxane when the terminal group on any one of $R^1$ to $R^6$, $R^9$ and $R^{10}$ is OH, an isocyanate functional siloxane when at least one of $R^1$ to $R^{10}$ bears at least one NCO or an epoxy functional siloxane when at least one of $R^1$ to $R^6$, $R^9$ and $R^{10}$ bears an epoxy. The integers x, y and z are selected so that the molecular weight of formula (I) is in the range of 200 to 500,000, 500 to 100,000 or 500 to 50,000.

The compound of formula (III) is an amino functional siloxane when the terminal group on any one of $R^{14}$ to $R^{19}$, $R^{22}$ $R^{23}$ is $NH_2$, a carbinol functional siloxane when the terminal group on any one of $R^{14}$ to $R^{19}$, $R^{22}$ and $R^{23}$ is OH, an isocyanate functional siloxane when at least one of $R^{14}$ to $R^{23}$ bears at least one NCO or an epoxy functional siloxane when at least one of $R^{14}$ to $R^{19}$, $R^{22}$ and $R^{23}$ bears an epoxy. The integers p, q and r are selected so that the molecular weight of formula (I) is in the range of 200 to 500,000, 500 to 100,000 or 500 to 50,000.

Amino functional siloxanes include those available from UCT Silanes such as PS510, PS512 and PS513 and those available from Gelest such as primary aminopropyl terminated siloxanes such as DMS-A11, DMS-A12, DMS-A15, DMS-A21, DMS-A31, DMS-A32, DMS-A35, secondary amino functional (N-ethylaminoisobutyl terminated PDMS) siloxanes such as DMS-A211, 214, aminopropylmethylsiloxane—dimethylsiloxane copolymers such as AMS-132, AMS-152, AMS-162, AMS-163, AMS-191, AMS-1203, aminoethylaminopropylmethylsiloxane—dimethylsiloxane copolymers such as AMS-233, AMS-2202, aminoethylaminoisobutylmethylsiloxane—dimethylsiloxane copolymers such as AMS-242 and ATM-1112, ATM-1322.

Carbinol functional siloxanes include those available from Gelest such as carbinol (hydroxyl) terminated polydimethylsiloxanes DMS-C15, DMS-C16, DMS-C21, DMS-C23, DMS-C25, DBL-C31, DBL-C32, [bis(hydroxyethyl)amine]terminated olydimethylsiloxanes such as DMS-CA21 and (carbinol functional) methylsiloxane-dimethylsiloxane copolymers such as CMS-221, CMS-222, CMS-832, CMS-626.

Epoxy functional siloxanes include those available from Gelest such as epoxypropoxypropyl terminated polydimethylsiloxanes including DMS-E range (09-21), epoxypropoxypropyl terminated polyphenylmethylsiloxanes such as PMS E-11, PMS E 15, monophenyl functional tris(epoxy terminated polydimethylsiloxane) such as MCT-EP13, mono-(2, 3-epoxy)propylether terminated polydimethylsiloxane such as MCR-E11, MCR-E21 and (epoxycyclohexylethyleethylsiloxane)—dimethylsiloxane dipolymers such as ECMS-127, 227, 327, 924.

Representative examples of aminosiloxanes include the following:

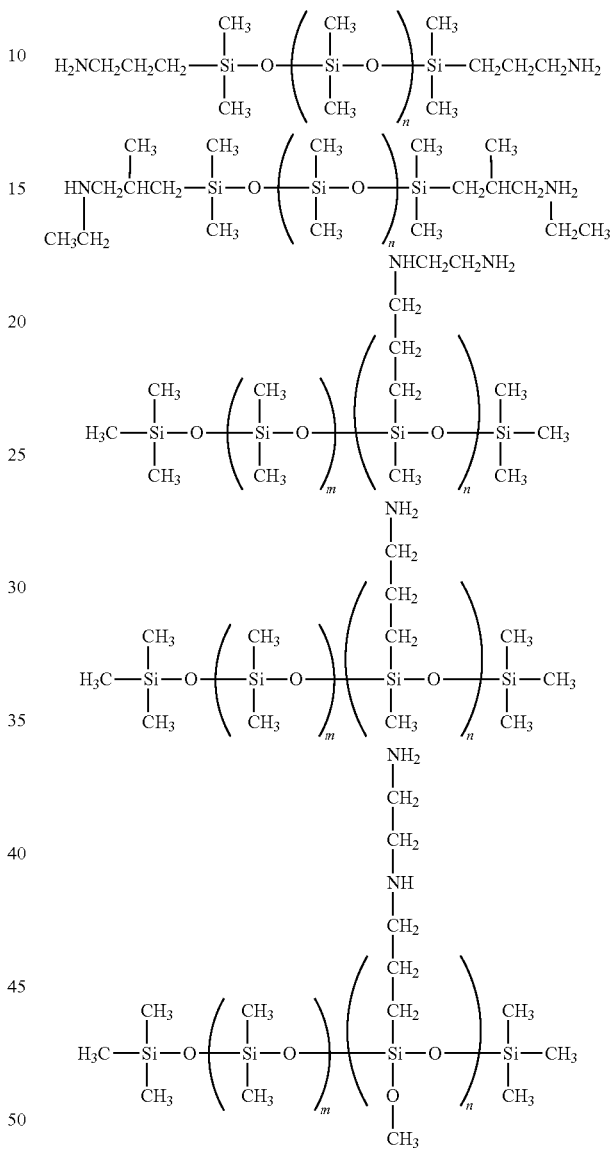

in which
m is 1-1500; and
n is 1-1500.

Representative examples of carbinol siloxanes include the following:

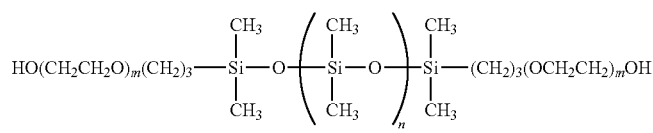

-continued

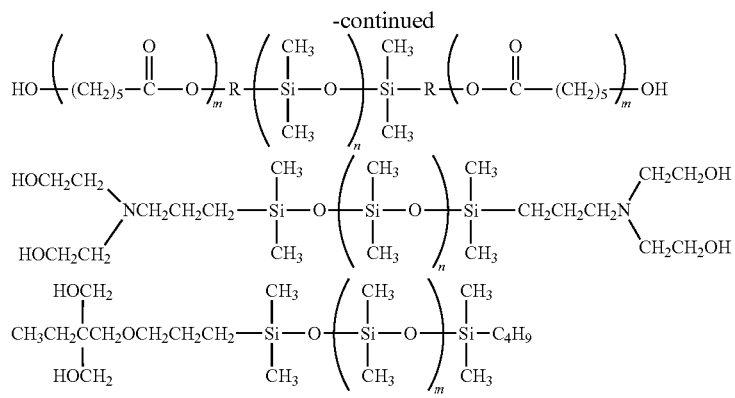

in which
m is 1-1500; and
n is 1-1500.

Representative examples of isocyanate siloxanes include the reaction product of:

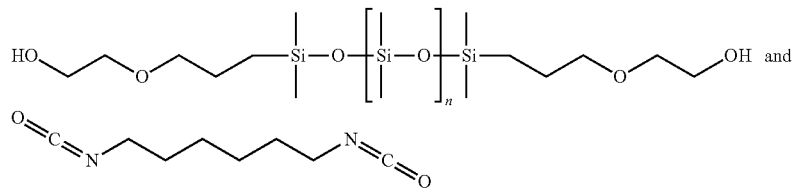

in which
n is 1-1500.

The compound of formula (II) or (III) may be present in an amount of 1-99% by weight, 10-80% by weight or 20-60% by weight based on the total weight of the polymer.

Polyisocyanates

Suitable polyisocyanates include any isocyanate typically used to form cross-linked coatings. The polyisocyanate may be a masked isocyanate which are compounds in which the isocyanate group or groups are generated usually by heating at 100 to 200° C. Masked isocyanates include those supplied by Chemtura Baxendon and the Bayhydur® range from Bayer. Blocking groups used to make masked isocyanates include ε-caprolcatome, methylethylketoxime, 3,5-dimethylpyrazole and diethyl malonate. The polyisocyanates may include diisocyanates, triisocyanates and higher functionality isocyanates.

Diisocyanates include but are not limited to 1,5-naphthalene diisocyanate, 4,4-diphenyl-methane diisocyanate, tetraalkyl-diphenyl methane diisocyanate, 1,3-phenylene diisocyanate, 1,4-phenylene diisocyanate, butane-1,4-diisocyanate, hexamethylene 1,6-diisocyanate, 2,2,4-trimethylhexamethylene 1,6-diisocyanate, 2,4,4-trimethylhexamethylene 1,6-diisocyanate, cyclohexane-1,4-diisocyanate, xylilene diisocyanate, dicyclohexyl-methane-4,4'-diisocyanate, methyl-cyclohexane diisocyanate, 1,4-tetramethylene diisocyanate, hexamethylene diisocyanate, 1,3-trimethylene diisocyanate, metaxylene diisocyanate, decamethylene 1,10-diisocyanate, cyclohexylene 1,2-diisocyanate, cyclohexylene 1,4-diisocyanate, 1-methyl cyclohexane 2,4-diisocyanate, 2,4-toluene diisocyanate, hexamethylene-1,6-diisocyanate, heptamethylene-1,7-diisocyanate, 1,3-cyclopentene diisocyanate and 1,3-cyclohexane diisocyanate.

Triisocyanates include trimers of isophorone diisocyanate, triisocyanato nonane, triphenylmethane triisocyanate, 1,3,5-benzene triisocyanate, 2,4,6-toluene triisocyanate, lysine triisocyanate, an adduct of trimethylol and tetramethyl xylene diisocyanate sold under the name Cythane® 3160 by Cytec Industries, and Desmodur® N 3300, which is the isocyanurate of hexamethylene diisocyanate, available from Bayer.

Polyisocyanates with higher functionality include but are not limited aliphatic polyisocyanates based on hexamethyldiisocyanate such as sold by Bayer under the Desmodur® N range, aliphatic polyisocyanates based on isophorondiisocyanate such as sold by Bayer under the Desmodur® Z range, aromatic polyisocyantes based on toluene diisocyante such as sold by Bayer under the Desmodur® L range, aromatic polyisocyanates based on methylendiphenyldiisocyanate such as sold by Bayer under the Desmodur® VL and VK range, blocked polyisocyanates such as those sold under the Desmodur® BL range and Basonet® isocyanate cross-linkers (Bayer).

Isocyanurate rings containing 3 or more isocyanate groups can also be used for example the isocyanurate ring of hexamethylene diisocyante such as Desmodur® N-3300 and N-3390 from Bayer.

The polyisocyanates may be used in combination with other isocyanates.

In one example, the polyisocyanate is a triisocyanate such as lysine triisocyanate or polyisocyanates sold by Bayer under the Desmodur® range.

The polyisocyanate may be present in an amount of 0.1-70% by weight, 0.5-50% by weight or 1-30% by weight based on the total weight of the polymer.

Polyol or Polyamine

Suitable polyols or polyamines include those typically used to form cross-linked coatings such as polyester polyols/polyamines, polyether polyols/polyamines, polycarbonate polyols/polyamines and acrylic polyols/polyamines. A mixture of polyols/polyamines can be used in formulating the polymer.

Polyols that may be used include polyester polyols such as Desmophen, Baycoll® (Bayer); polyether polyols such as Desmophene® and Acclaim®; polyaspartics such as Desmophen® NH; polycarbonate polyols such as Desmophen® C, as well as polymer cross-linkers such as poly(caprolactone) which contain multiple arms, as well as the polyol base component of Desothane® HS Clear Topcoat CA 8000/B900A (PPG Aerospace).

Suitable polyamines include but are not limited to primary amines and mixtures thereof including polyamines having at least two functional groups such as di-, tri- or higher functional polyamines and mixtures thereof. The polyamine may be aromatic or aliphatic, such as cycloaliphatic.

Examples of suitable aliphatic polyamines include but are not limited to ethylene diamine, 1,2-diaminopropane, 1,4-diaminobutane, 1,3-diaminopentane (Dytek EP, Invista), 1,6-diaminohexane, 2-methyl-1,5-pentane diamine (Dytek A, Invista), 2,5-diamino-2,5-dimethylhexane, 2,2,4- and/or 2,4,4-trimethyl-1,6-diamino-hexane, 1,11-diaminoundecane, 1,12-diaminododecane, 1,3- and/or 1,4-cyclohexane diamine, 1-amino trimethyl-8-aminomethyl-cyclohexane, 2,4- and/or 2,6-hexahydrotoluylene diamine, 2,4'-diaminodicyclohexyl methane, 4,4'-diaminodicyclohexyl methane (PACM-20, Air Products) and 3,3'-dialkyl 4,4'-diaminodicyclohexyl methanes such as 3,3'-dimethyl-4,4'-diaminodicyclohexyl methane (Dimethyl Dicykan® or Laromin® C260, BASF; Ancamine® 2049, Air Products) and 3,3'-diethyl-4,4'-diaminodicyclohexyl methane), 2,4- and/or 2,6-diaminotoluene and 2,4'- and/or 4,4'-diaminodiphenyl methane, or mixtures thereof. Other suitable amines include but are not limited to 3-(cyclohexylamine) propylamine, 3,3'-[1,4-butanediylbis]-1-propanamine and diamino functional polyetheramines having aliphatically bound primary amino groups, examples of which include Jeffamine® D-230, Jeffamine® D-400, Jeffamine® D-2000, and Jeffamine® D-4000 available from Huntsman Corporation.

In certain examples, the polyamine is a triamine. Examples of suitable triamines include dipropylene triamine, bis(hexamethylene) triamine and triamino functional polyetherpolyamines having aliphatically bound primary amino groups (Jeffamine® T-403, Jeffamine® T-3000, Jeffamine® T-5000 from Huntsman Corporation.)

In other examples, the amine can be a tetraamine or other higher functional amine.

The molecular weight of the polyol/polyamine may be in the range of 46-10000, 46-1000 or 46-100.

The polyol/polyamine may be present in an amount of 0-99% by weight, 0-50% by weight or 5-30% by weight based on the total weight of the polymer.

Reactive Coating

The reactive coating may be any coating containing a polyisocyanate and/or a polyol or polyamine. Examples include existing polyurethane, polyurea, polysilicone, polyester or epoxy coatings which contain a polyisocyanate and/or a polyol or polyamine. Polyol containing coatings also include coatings containing hydroxyl polyesters. Specific examples include polyurethane coatings containing polyols such as Desothane® HS Clear Topcoat CA 8000/B900A available from PPG Aerospace or Eclipse® ECL-G-2 or Eclipse® ECL-G-7 or Aerodur 3002 Clear coat from AkzoNobel Aerospace Coatings.

Surface

The surface on which the polymer coating is applied on may be an uncoated surface of an object or an object having an existing coating. The existing coating may be one or more layers of a coating selected from primers, conversion coatings, topcoats etc. The polymer coating may be applied on an object painted with a topcoat. Alternatively, the polymer may be mixed into a topcoat and applied on an object having a primer, a conversion coating or other coating. In the latter instance, the polymer forms part of the topcoat. Preferably, the existing coating or the topcoat is a polyurethane, polyurea, polysilicone, polyester or epoxy coating.

Solvents

The solvent used in the polymer formulation may be a single solvent or a combination of two or more solvents. Preferably the solvent is an organic solvent. Suitable organic solvents or solvent combinations include but are not limited to:

(a) ester based solvents such as alkyl propionate, alkoxypropionate, alkyl alkoxypropionate, alkyl acetate, alkyl alkoxyacetate, ethyl acetate, propyl acetate, isopropyl acetate, butyl acetate, isobutyl acetate, tertiary butyl acetate and glycol ether acetates;

(b) ketones such as alkyl ketones for example, methyl ethyl ketone, methyl propyl ketone, methyl amyl ketone, methyl isoamyl ketone and methyl isobutyl ketone, acetone, pentanone, butanone and 2-heptanone;

(c) aromatics such as toluene and xylene;

(d) ethers such as glycol diethers, for example, the di-Ci-s alkyl ethers of glycols such as diethers of ethylene glycol, diethylene glycol, triethylene glycol, tetraethylene glycol polyethylene glycol, propylene glycol, dipropylene glycol, tripropylene glycol and polypropylene glycol including but not limited to diethylene glycol dimethylether, dipropylene glycol dimethyl ether or methyl butylether of diethylene glycol such as those marketed by Dow under the trade name Downanol E-series and P-series glycolethers; and cyclic ethers such as tetrahydrofuran; and (e) halogenated solvents such as dichloromethane and tetrachloroethylene;

In view of the toxicity and negative environmental impact of halogenated solvents, it will be understood that they should be used within the constraints of environmental, health and safety regulations. Preferred solvents are ester based solvents such as alkyl propionate, alkoxypropionate, alkyl alkoxypropionate, alkyl acetate, alkyl alkoxyacetate, ethyl acetate, propyl acetate, isopropyl acetate, butyl acetate, isobutyl acetate, tertiary butyl acetate and glycol ether acetates; ketone solvents such alkyl ketones for example, methyl ethyl ketone, methyl propyl ketone, methyl amyl ketone, methyl isoamyl ketone and methyl isobutyl ketone, acetone, pentanone, butanone and 2-heptanone.

Additives

The polymer formulation can additionally include a variety of optional additives that are somewhat dependent on the particular application of the coating such as curing agents, cross-linking agents, catalysts, fillers, pigments or other colorants, reinforcements, thixotropes, accelerators, surfactants, plasticizers, extenders, stabilizers, corrosion inhibitors, hindered amine light stabilizers, UV light absorbers and antioxidants. Preferable additives may include extenders, catalysts and cross-linking agents.

In one example, the polymer comprises or consists of the reaction product of the siloxane prepolymer of formula (II) and (i) a reactive coating and optionally a polyisocyanate and/or a polyol or polyamine or (ii) a polyisocyanate and optionally a polyol or a polyamine or (iii) a polyol or polyamine and optionally a polyisocyanate.

In another example, the polymer comprises or consists of the reaction product of the isocyanate prepolymer of formula (I) and (i) a polysiloxane and optionally a polyol or a polyamine.

The polymer formulation comprises or consists of the polymer, a solvent, an optional extender, an optional catalyst or an optional cross-linking agent.

Examples of extenders include pot-life extenders such as 2,4-pentanedione and alkyl acetoacetate.

Examples of catalysts include metal catalysts such as dibutyltin dilaurate, stannous octotate, lead carbonate, lead octoate, ferric acetylacetonate, and alkali-metal salts.

Examples of cross-linking agents include multifunctional polymers such as star shaped or multi-armed polymers with functionality capable of reacting with the existing coating such as hydroxyl, isocyanate or amine.

The additives are present in an amount of 0-80% by weight such as 1-70% by weight or 5-60% by weight based on the total weight of the polymer.

Polymers

Exemplary polymers include those which are reaction products of the following combinations:
  (a) FPOSS siloxane prepolymer with at least one terminal amino group, polyisocyanate and optionally a catalyst, polyol or polyamine;
  (b) FPOSS siloxane prepolymer with at least one terminal hydroxy group, polyisocyanate and optionally a catalyst, polyol or polyamine;
  (c) FPOSS siloxane prepolymer with at least one terminal amino group or FPOSS siloxane prepolymer with at least one terminal hydroxy group, a reactive coating and optionally a catalyst, polyol or polyamine;
  (d) FPOSS siloxane prepolymer with at least one isocyanate, polysiloxane and optionally a catalyst, polyol or polyamine; and
  (e) FPOSS polyisocyanate prepolymer, polysiloxane and optionally a catalyst.

Polymer Formulation

The polymer formulation may be made by dissolving the compound of formula (I) or (II) in an organic solvent such as a ketone for example 2-heptanone (MAK) prior to reaction with a polyisocyanate and/or a polyol, a polyamine or a reactive coating. The polyisocyanate and/or polyol or polyamine may also be dissolved in ketone, ether or ester based organic solvents prior to reaction with compound of formula (I) or (II). The polymer formulation is typically mixed for 15-120 minutes prior to applying on a surface.

The polymer formulation may optionally include the additives described above, in particular extenders, catalysts and/or cross-linking agents. A catalyst such as dibutyltin dilaurate may be required for the reaction between the compound of formula (I) or (II), the polyisocyanate and/or the polyol, polyamine, or the reactive coating.

Uses

The polymer formulation may be applied as a continuous coating upon a wide variety of surfaces, particularly metal surfaces such as aluminium, stainless steel or titanium. The polymer formulation may also be suitably applied to painted surfaces or to composite surfaces such as resin matrices of carbon, glass fibers or plastics and the like. The polymer formulation may also be applied to coated surfaces and as such independent of the base material of the surface.

The polymer formulation may be applied to a surface of an object in a number of ways. For instance, it may be applied to a surface by simply spraying the polymer formulation upon a surface. As a one component spray, a formulation of the polymer in a solvent is sprayed onto a surface to be coated. In the event a catalyst is required, the polymer and solvent would be mixed with the catalyst prior to use. The resultant formulation may have a finite pot life and would have to be sprayed soon after the catalyst is mixed or during the pot life of the mixture.

As a two component system, the compound of formula (I) or (II) may be dissolved in a solvent and the second component which is a polysiloxane (when formula I is used) or polyisocyanate (when formula II is used) and optionally the polyol or the polyamine dissolved separately in a solvent. Alternatively a reactive coating is used in place of the second component. The two mixtures are combined in a common spray nozzle and mixed while being sprayed onto a dry surface to form a polymer coating on the surface of an object.

Once the polymer has been allowed to sufficiently cross-link and the solvent evaporates, a film of polymer is left behind.

Alternatively, the compound of formula (I) or (II) is mixed with a solution of the polysiloxane or polyisocyanate and optionally the polyol, the polyamine or the reactive coating at a mixing nozzle of a spray gun and ejected onto the surface or mixed in a pot, transferred to a spray gun and ejected onto the surface prior to reaching the pot life of the mixture. This process results in a cross-linked polymer, which begins to cure within a few minutes and subsequently forms a cross-linked film.

Other methods of application can also be used such as those commonly known to those in the art such as by brush, roller, dip, droplet impact, printing, such as screen printing, or via a pre-packaged aerosol. The formulation may be applied as an appliqué by first depositing the formulation, as described above, upon a relief surface. When dry, the polymer coating may be removed from the relief surface and used in an appliqué process to adhere the coating onto a subsequent surface.

In a one component spray, the polymer is capable of being handled or walked upon as soon as the polymer has been allowed to sufficiently cross-link and the solvent has evaporated. Secondary process could include operations such as masking, taping and application of additional layers of the polymer coating. Use of a heat source, such as hot air or infrared lamps, will accelerate the solvent removal and the cross-linking reaction. In the two component system, the polymer starts to cross-link and form almost as soon as the two parts are mixed and sprayed onto the surface. Again use of hot air or heat lamps will facilitate solvent removal and cross-linking to leave behind a polymer coating in the form of a film.

The polymer coating may be in the form of a clear coating film and may be applied onto a wide variety of surfaces, including painted surfaces. A key advantage of a clear film coating is that it provides sufficient transparency to allow the coating to be used with a pigmented topcoat. A key advantage of a clear film coating is that it provides sufficient transparency to allow the coating to be used over a pigmented (coloured) topcoat for example in the formation of basecoat—clear coat coatings known to those in the art. Alternatively, the polymer coating may be pigmented by mixture of one or more of the reaction components with a suitable pigment in a colloid mill. The clear coating or pigmented coating may then be used as a paint.

The polymer formulation can be applied anywhere between about 1° C. and about 45° C. Typically, the polymer coating is applied at ambient temperatures, preferably between about 15° C. and 35° C. The polymer formulation may be applied to form a single layer or as multiple layers to achieve a desired thickness.

The polymer formulation may be applied as a continuous coating upon a wide variety of object surfaces, particularly metal surfaces such as aluminium, stainless steel or titanium, or to composite surfaces such as resin matrices of carbon or glass fibers, plastics and the like. The polymer may also be applied to coated surfaces and as such independent of the base material used in object. The polymer coating may be used to reduce the amount of ice forming on a surface and/or the adhesion of ice to the object's surface; for example upon the lift, stabilizing, and control surfaces of an aircraft. In this instance the entire surface of an aircraft may be coated with the polymer or just the lift, stabilizing, and/or control surfaces or other selected surfaces may be coated. Reduction of ice formation is of critical importance because even a slight build-up of ice upon the wings or other lift surfaces of the aircraft can cause dramatic alterations in the aerodynamic performance of the lift surfaces. Similarly, control surfaces of the aircraft must remain free of ice build-up which could block the movement and impair the option of those control surfaces. Additionally, reduction of ice formation reduces the overall weight of the aircraft, thereby improving performance, and fuel efficiency. Similar advantages are provided by coating at least some portions of the outer surface of other objects such as missiles, ships, automobiles and wind turbines.

The usefulness of the polymer is not limited to metal surfaces. The polymer finds use as a coating on any of a wide variety of surfaces such as carbon composites, and even wood or asphalt, a number of which may be applications unrelated to aircraft such as wind turbines, air conditioners, refrigeration units, buildings, signs and power lines.

Properties

When the polymer used as an ice reducing coating on a surface, the coated surface can demonstrate a minimum average adhesion force of <5 N when subjected to the ice adhesion test, a pencil hardness value of up to 4H and a 60 degree glass value of up to 75.

EXAMPLES

The invention will now be described with reference to the following non-limiting examples.

The following abbreviations are used in the examples:

Amino siloxane: PS510, PS412, PS513, and DMS A12

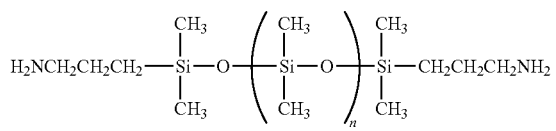

n is 5-1500

Lysine Triisocyanate

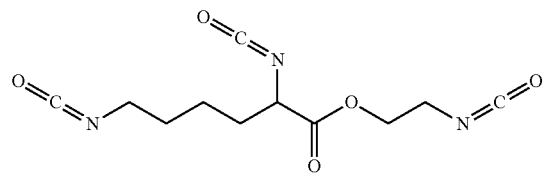 [SMILES: O=C=NCCCCC(N=C=O)C(=O)OCCN=C=O]

F-POSS-siloxane prepolymer prepared by reacting:

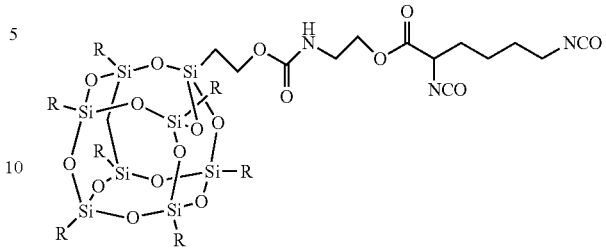

in which

R is as defined in formula (II) above; and

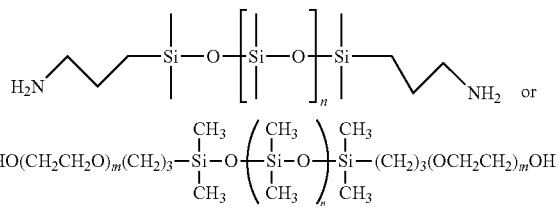

n is 5-1500; and m is 1-20

The details of the polymer formulations are set out in Table 1 below with reference to the following:

1. Solvent MAK (2-heptanone, methylamyl ketone) was used in all formulations in the examples and makes up between 30-85% weight of total formulation.
2. Mole ratio of 1:1 (reactive siloxane groups:isocyanate groups) used in all formulations.
3. All formulations were applied onto aluminium panels which had previously been coated with primer and an existing clear coat (Desothane® HS Clear Topcoat CA 8000/B900A) via a spray gun and then cured at ambient conditions for 12-24 hours.

The FPOSS containing reactive siloxane prepolymer is mixed in a solvent such as ketone, alcohol or ester. The isocyanate component is then added to the formulation and the solution mixed for 15-120 minutes prior to spray or brush application of the polymer coating on a surface.

Ice Adhesion Test Method

Ice adhesion was measured using an Instron Universal Testing Machine (model 5565) fitted with a 100 N load cell. Tests were carried out at a speed of 0.5 mm/min inside an environmental chamber that is maintained at −20° C. and located within the Instron. The polymer coating was applied to aluminium coupons and water (ultra-pure Milli-Q resistivity value of 18.2 MΩ·cm @ 25° C.; ≤5 ppb) filled cylindrical columns were frozen at −20° C. onto the surface. A pendulum attachment is fitted to the Instron and the ice columns and a tensile force was applied to dislodge the ice columns from the coated specimens. The tensile force required to separate ice was recorded and the stress calculated. The mode of failure—cohesive or adhesive was also noted.

TABLE 1

| Number | Siloxane Reactive group | Siloxane Molecular weight | Isocyanate | % F-POSS siloxane prepolymer (FIG. 3) (Mw 23,370) | Polyol/ polyamine | Solvent |
|---|---|---|---|---|---|---|
| Desothane HS Clear Topcoat CA 8000/B900A (PPG)* | — | — | Desothane Activator^ | — | Desothane Base^^ | Proprietary mix of solvents including 2,6-dimethyl-4-heptanone, 4,6-dimethyl-2-heptanone, methyl amyl ketone, 2,4-pentanedione ethyl acetate, N-butyl acetate and 1,2,4-trimethyl benzene |
| 1 | — | — | Lysine triisocyanate | 100% | — | 2-heptanone |
| 2 | — | — | Desothane Activator^ | 2% | Desothane Base^^ | 2-heptanone |
| 3 | — | — | Desothane Activator^ | 5% | Desothane Base^^ | 2-heptanone |
| 4 | — | — | Desothane Activator^ | 10% | Desothane Base^^ | 2-heptanone |
| 5 | Amino (PS510) | 2500 | Lysine triisocyanate | 4% | — | 2-heptanone |
| 6 | Amino (PS510) | 2500 | Lysine triisocyanate | 10% | — | 2-heptanone |
| 7 | Amino (PS510) | 2500 | Desothane Activator^ | 4% | — | 2-heptanone |
| 8 | | | Desothane Activator^ | 2% | Desothane Base^^ | F-POSS-siloxane added as 50% solution in 2-heptanone (scaled up formulation) |

*Comparative example
Note:
^^Desothane HS Clear Topcoat CA 8000/B900A Base: Base CA 8000/B900A (PPG Aerospace)

Surface Energy Testing Method
Surface Energy calculations are based on contact angle measurements complete using 'FIRST TEN ANGSTROMS' semi-automated video equipped contact angle analyser. Diiodomethane ($CH_2I_2$) and water ($H_2O$) were employed as the reference solvents to calculate the dispersive and polar contributions to surface energy through the Young-Dupre relationship and Fowkes equation.

Gloss Test Method
Gloss is measured on a Byk-Gardner micro-TRI gloss meter at 20 and 60°.

Pencil Hardness Test Method
Pencil hardness is measured according to ASTM D3363.

TABLE 2

| Example | Ice Adhesion-Tensile Force (N) | Ice Adhesion-Tensile Stress (kPa) | Failure Mode** |
|---|---|---|---|
| Desothane HS CA 8000 B900A Clearcoat* | 45 ± 14.3 | 176.7 ± 56.1 | 40% CF 60% AF |
| NuSil R1082* | 11.6 ± 4.4 | 45.7 ± 17.1 | 100% AF |
| NuSil R2180* | 16.5 ± 3.1 | 64.7 ± 12.3 | 100% AF |
| U.S. Pat. No. 6,797,795* (Example 1) | 5.2 ± 2.6 | 20.3 ± 10.3 | 100% AF |
| U.S. Pat. No. 7,910,683* (Example 3) | 10.4 ± 5.9 | 40.9 ± 23.1 | 100% AF |
| 1 | 3.1 ± 3.5 | 12.3 ± 13.9 | 100% AF |
| 2 | 26.1 ± 10.6 | 102.4 ± 41.5 | 90% AF; 10% CF |
| 3 | 10.4 ± 3.2 | 40.9 ± 12.6 | 100% AF |
| 4 | 21.6 ± 16.5 | 85.0 ± 64.8 | 85% AF, 15% CF |
| 5 | 4.9 ± 3.4 | 19.3 ± 13.3 | 100% AF |
| 6 | 5.6 ± 2.9 | 22 ± 11.2 | 100% AF |
| 7 | 8.2 ± 2 | 32 ± 8 | 100% AF |
| 8 | 17.5 ± 4.9 | 69 ± 19 | 99% AF, 1% CF |

*Comparative example
**AF = adhesive failure, CF = Cohesive failure

TABLE 3

| Example | $H_2O$ Contact Angle (°) | $CH_2I_2$ Contact Angle (°) | Surface ENERGY Dispersion (mJ/m²) | Surface Energy Polar (mJ/m²) | Gloss 20° | Gloss 60° | Pencil Hardness (Gauge) |
|---|---|---|---|---|---|---|---|
| Desothane HS CA 8000 B900A Clearcoat* | 82.2 | 39.8 | 41.6 | 2.5 | 86 | 95 | 4H |

TABLE 3-continued

| Example | H₂O Contact Angle (°) | CH₂I₂ Contact Angle (°) | Surface ENERGY Dispersion (mJ/m²) | Surface Energy Polar (mJ/m²) | Gloss 20° | Gloss 60° | Pencil Hardness (Gauge) |
|---|---|---|---|---|---|---|---|
| NuSil R1082* | 109.0 | 62.2 | 28.6 | 0 | 30 | 66 | HB |
| NuSil R2180* | 110.1 | 61.5 | 29.1 | 0 | 27 | 57 | HB |
| U.S. Pat. No. 6,797,795* (Example 1) | 106.2 | 63.6 | 27.7 | 0.05 | 18 | 53 | <6B tacky |
| U.S. Pat. No. 7,910,683* (Example 3) | 127.8 | 104.4 | 7.5 | 0.03 | 44 | 68 | <6B tacky |
| 1 | 108.2 | 74.5 | 21.3 | 0.23 | 35 | 69 | H |
| 2 | 103.7 | 69.2 | 24.4 | 0.43 | 38 | 69 | 4H |
| 3 | 106.3 | 54.9 | 27 | 0.07 | 46 | 72 | H |
| 4 | 107.8 | 69.6 | 24.2 | 0.10 | 42 | 68 | 2H |
| 5 | 103.3 | 63.3 | 28 | 0.22 | 48 | 73 | 4H |
| 6 | 104.6 | 62.9 | 28.2 | 0.12 | 55 | 75 | H |
| 7 | 106.5 | 63.8 | 27.6 | 0 | 50 | 73 | B |
| 8 | 103.2 | 71.2 | 23.2 | 0.6 | 49 | 74 | 3H |

*Comparative example

Cross-linked FPOSS containing polysiloxane prepolymer based on urea and urethane cross-linked chemistry was found to be compatible with current aircraft polyurethane topcoat and can be used alone as a thin final top layer or as a component of the current topcoat to provide a polymer coating with reduced ice adhesion. Two commercially available NuSil polysiloxane elastomer coatings, and two coating formulations disclosed in Example 1 of U.S. Pat. No. 6,797,795 and Example 3 of U.S. Pat. No. 7,910,683 which do not contain FPOSS all have ice adhesion tensile stress values of greater than 19 kPa.

The present polymer coatings demonstrate the following advantages:

(i) Reduced ice adhesion<19 kPa stress, or <5 N force, which is less than previously published values for ice adhesion; and (ii) Pencil Hardness values above commercially available siloxane hardness materials such as those from NuSil and much higher than existing art such as U.S. Pat. No. 6,797,795.

(iii) 60 degree gloss values up to 75, demonstrating higher gloss than commercially available siloxane coating materials such as NuSil; and (iv) Improved compatibility to existing polyurethane topcoat for aircraft application and the polymer coating formulation can be used as a component of the existing polyurethane topcoat.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various examples.

It will be understood to persons skilled in the art that many modifications may be made without departing from the spirit and scope of the invention.

Columns 11-12, Lines 3-65, replace the representative example with the following representative example:
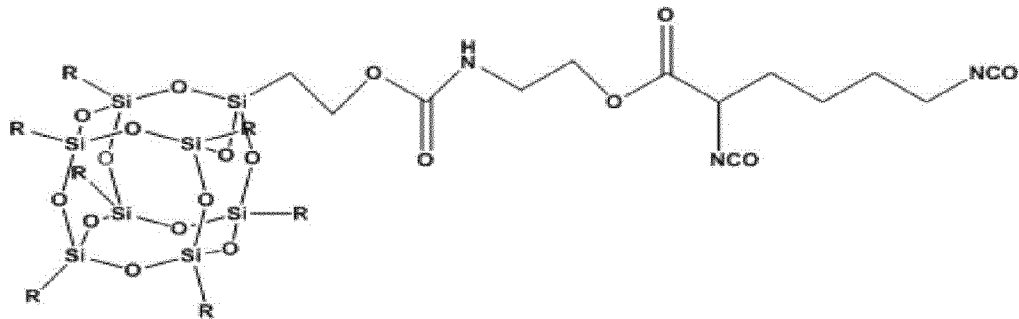
and
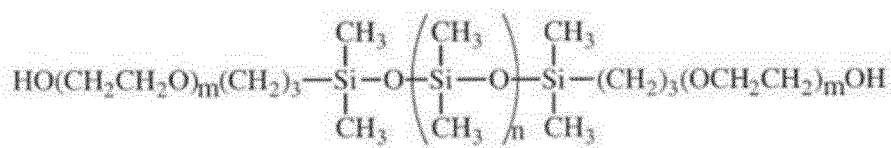
or
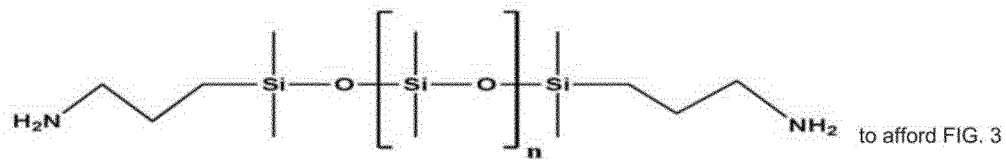
to afford FIG. 3
Column 24, Lines 1-14, replace the compound with the following compound:
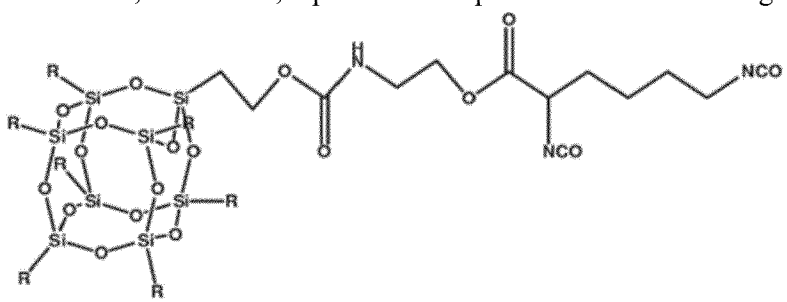
In the Claims
Column 28, Claim 1, Lines 25-35, replace Formula (I) with the following Formula (I):
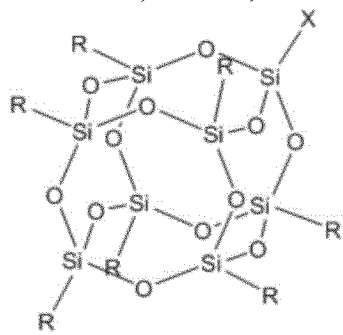

Column 29, Claim 2, Lines 31-39, replace Formula (I) with the following Formula (I):
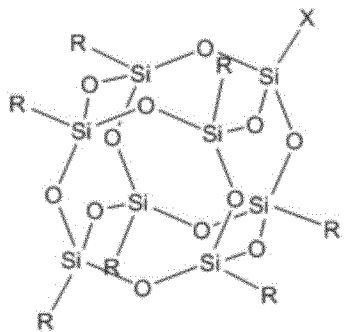

The invention claimed is:

1. An FPOSS polyisocyanate prepolymer of the formula (I):

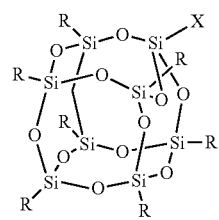

in which X is $(CH_2)_2OC(O)NH(CH_2)_2OC(O)CH(NCO)(CH_2)_4NCO$ or optionally substituted $C_{1-20}$alkyl comprising at least two isocyanate groups and which may be optionally interrupted by O, $CH_2O$, Si, NH, $NR^{11}$, C=O, CH(OH), NH, CR(NCO), $(CH_2)_n$, or $CO_2$;

R is independently selected from a polyisocyanate, an optionally substituted $C_{1-20}$alkyl which may be optionally interrupted with O, C=O, N=C=O, CH(OH), $CH_2OR^{11}$, $CH_2SR^{11}$, or $(CH_2)_m(CF_2)_nCF_3$, provided that at least one R is $(CH_2)_m(CF_2)_nCF_3$;

m is 1 to 20;

n is 0 to 20; and $R^{11}$ is H or optionally substituted $C_{1-16}$ alkyl.

2. An FPOSS siloxane prepolymer of the formula (II):

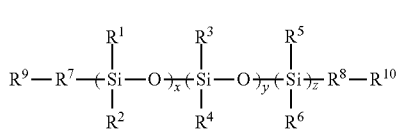

in which $R^1$ to $R^6$ are independently selected from the group consisting of H; optionally substituted $C_{1-16}$alkyl optionally interrupted with a group selected from $NR^{11}$, C=O, C=C, S, $CO_2$, O and CH(NCO); $OSiR^{12}_3$; $(CH_2)_nOH$; $(CH_2)_nO(CH_2)_nOH$; $(CH_2)_nNR^{11}R^{12}$; $(CH_2)_nNH(CH_2)_nNR^{11}R^{12}$; $(CH_2)_nO(CH_2)_n$; $NR^{11}R^{12}$; $(CH_2)_nNCO$; epoxy; $(CH_2)_n$FPOSS of formula (I), optionally substituted $C_{1-16}$alkylaryl; optionally substituted aryl; optionally substituted polyaryl; optionally substituted $C_{3-6}$cycloaliphatic; and optionally substituted $C_{3-6}$heterocyclyl;

$R^7$ and $R^8$ are independently absent or independently selected from the group consisting of optionally substituted $C_{1-16}$alkyl optionally interrupted with a group selected from $NR^{11}$, C=O, C=C, S, $CO_2$, O and CH(NCO); O; S; $OSi(R^{13})_2$; $(CH_2)_n$; $(CH_2)_n$NH; $(CH_2)_n$ O; optionally substituted $C_{1-16}$alkylaryl; optionally substituted aryl; optionally substituted polyaryl; optionally substituted $C_{3-6}$cycloaliphatic; and optionally substituted $C_{3-6}$heterocyclyl;

$R^9$ and $R^{10}$ are independently selected from the group consisting of H, OH, $NR^{11}R^{12}$, optionally substituted $C_{1-16}$alkyl, NCO, epoxy, $Si(R^{13})_3$ and FPOSS of formula (I);

$R^{11}$ and $R^{12}$ are independently selected from the group consisting of H and optionally substituted $C_{1-16}$alkyl;

$R^{13}$ is selected from the group consisting of optionally substituted $C_{1-16}$alkyl, $(CH_2)_n$OH and $(CH_2)_n$NH$_2$;

n is 1 to 16;

x and z are independently selected from 1 to 1500; and y is 0 to 1500;

with the proviso that at least one of $R^1$ to $R^6$, $R^9$ and $R^{10}$ is the FPOSS polyisocyanate prepolymer of the formula (I), and wherein the FPOSS polyisocyanate prepolymer of the formula (I) is:

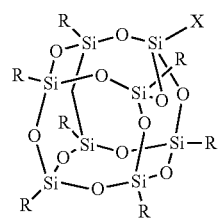

(I)

in which

X is $(CH_2)_2OC(O)NH(CH_2)_2OC(O)CH(NHCOY)$ $(CH_2)_4NHCOY'$, $(CH_2)_nOY$, $(CH_2)_nNHY$ or optionally substituted $(CH_2)_mY$ which may be interrupted with O, $CH_2$O, Si, NH, $NR^{11}$, C=O, CH(OH), NH, CR(NCO), $(CH_2)_n$ or $CO_2$;

Y and Y' denote positions at which the FPOSS polyisocyanate prepolymer of formula (I) can be linked to the same or different FPOSS siloxane prepolymer of formula (II) and R, m, n and $R^{11}$ are as defined in formula (I);

R is independently selected from a polyisocyanate, an optionally substituted $C_{1-20}$alkyl which may be optionally interrupted with O, C=O, N=C=O, CH(OH), $CH_2OR^{11}$, or $(CH_2)_m(CF_2)_nCF_3$, provided that at least one R is $(CH_2)_m(CF_2)_nCF_3$;

m is 1 to 20; and n is 0 to 20.

3. The FPOSS siloxane prepolymer according to claim 2, wherein the FPOSS prepolymer of Formula (I) is linked at the Y position to a first siloxane prepolymer of Formula (II) and to a second siloxane prepolymer of Formula (II) at the Y' position.

4. The FPOSS siloxane prepolymer according to claim 3, wherein the ratio of FPOSS prepolymer of Formula (I) to siloxane prepolymer of Formula (II) is about 1:2 to 14:15 respectively.

5. The FPOSS siloxane prepolymer according to claim 4, wherein the ratio of FPOSS prepolymer of Formula (I) to siloxane prepolymer of Formula (II) is about 2:3 respectively.

6. A polymer comprising a cross-linked reaction product of the following:

the FPOSS polyisocyanate prepolymer of the formula (I) according to claim 1 and one or more of a polysiloxane of formula (III):

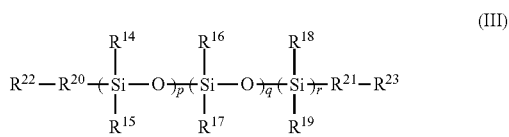

(III)

in which $R^{14}$ to $R^{19}$ are independently selected from the group consisting of hydrogen; optionally substituted $C_{1-16}$alkyl optionally interrupted with a group selected from $NR^{24}$, C=O, C=C, S, $CO_2$, O and CH(NCO); $OSiR^{25}_3$, $(CH_2)_n$OH; $(CH_2)_nO(CH_2)_n$OH; $(CH_2)_n$ $NR^{24}R^{25}$; $(CH_2)_nNH(CH_2)_n$ $NR^{24}R^{25}$; $(CH_2)_nO(CH_2)_n$ $NR^{24}R^{25}$; $(CH_2)_n$NCO; epoxy; optionally substituted $C_{1-16}$alkylaryl; optionally substituted aryl; optionally substituted polyaryl; optionally substituted $C_{3-6}$cycloaliphatic; and optionally substituted $C_{3-6}$heterocyclyl;

$R^{20}$ and $R^{21}$ are independently absent or independently selected from the group consisting of optionally substituted $C_{1-16}$ alkyl optionally interrupted with a group selected from $NR^{24}$, C=O, C=C, S, $CO_2$, O and CH(NCO); O; S; $OSi(R^{26})_2$; $(CH_2)_n$; $(CH_2)_n$NH; $(CH_2)_n$O; optionally substituted $C_{1-16}$alkylaryl; optionally substituted aryl; optionally substituted polyaryl; optionally substituted $C_{3-6}$cycloaliphatic; and optionally substituted $C_{3-6}$heterocyclyl;

$R^{22}$ and $R^{23}$ are independently selected from the group consisting of H, OH, $NR^{11}R^{12}$, optionally substituted $C_{1-16}$alkyl, NCO, epoxy and $Si(R^{13})_3$;

$R^{24}$ and $R^{25}$ are independently selected from the group consisting of H and optionally substituted $C_{1-16}$alkyl;

$R^{26}$ is selected from the group consisting of optionally substituted $C_{1-16}$alkyl, $(CH_2)_n$OH and $(CH_2)_n$NH$_2$;

n is 1 to 16;

p and r are independently selected from 1 to 1500;

q is 0 to 1500; and optionally at least one of a polyol, a polyamine, a polyisocyanate, and a reactive coating.

7. The polymer according to claim 6, wherein the FPOSS prepolymer of Formula (I) is linked at the Y position to a first polysiloxane of Formula (III) and to a second polysiloxane of Formula (III) at the Y' position.

8. The polymer according to claim 7, wherein the ratio of FPOSS prepolymer of Formula (I) to polysiloxane of Formula (III) is about 1:2 to 14:15 respectively.

9. The polymer according to claim 8, wherein the ratio of FPOSS prepolymer of Formula (I) to polysiloxane of Formula (III) is about 2:3 respectively.

10. The polymer according to claim 6 in which the polyisocyanate is a diisocyanate, triisocyanate, higher functionality isocyanate or a combination thereof.

11. The polymer according to claim 6 in which the polyisocyanate is present in an amount of 0.1-70% by weight based on the total weight of the polymer.

12. The polymer according to claim 6 in which the polyol or polyamine is a polyester polyol/polyamine, a polyether polyol/polyamine, a polycarbonate polyol/polyamine, an acrylic polyol polyamine or a combination thereof.

13. The polymer according to claim 6 in which the polyamine is present in an amount of 0-99% by weight based on the total weight of the polymer.

14. The polymer according to claim 6 in which the reactive coating is a polyurethane, polyurea, polysilicone, polyester or epoxy coating, each of which contain a polyisocyanate and/or a polyol or polyamine.

15. A polymer formulation comprising the polymer according to claim 6, a solvent and an optional additive.

16. An object comprising an external surface in which at least a portion of the external surface is coated with the polymer according to claim 6.

17. A method of imparting ice reducing properties to at least a portion of an external surface of an object comprising applying a coating comprising the polymer according to claim 6.

18. A polymer comprising a cross-linked reaction product of:
the FPOSS siloxane prepolymer of the formula (II) according to claim 2;
a polysiloxane of formula (III):

$$R^{22}-R^{20}-(\text{Si}(R^{14})(R^{15})-O)_p-(\text{Si}(R^{16})(R^{17})-O)_q-(\text{Si}(R^{18})(R^{19}))_r-R^{21}-R^{23} \quad (III)$$

in which
$R^{14}$ to $R^{19}$ are independently selected from the group consisting of hydrogen; optionally substituted $C_{1-16}$alkyl optionally interrupted with a group selected from $NR^{24}$, C=O, C=C, S, $CO_2$, O and CH(NCO); $OSiR^{25}_3$; $(CH_2)_nOH$; $(CH_2)_nO(CH_2)_nOH$; $(CH_2)_nNR^{24}R^{25}$; $(CH_2)_nNH(CH_2)_nNR^{24}R^{25}$; $(CH_2)_nO(CH_2)_nNR^{24}R^{25}$; $(CH_2)_nNCO$; epoxy; optionally substituted $C_{1-16}$alkylaryl; optionally substituted aryl; optionally substituted polyaryl; optionally substituted $C_{3-6}$cycloaliphatic; and optionally substituted $C_{3-6}$heterocyclyl;

$R^{20}$ and $R^{21}$ are independently absent or independently selected from the group consisting of optionally substituted $C_{1-16}$ alkyl optionally interrupted with a group selected from $NR^{24}$, C=O, C=C, S, $CO_2$, O and CH(NCO); O; S; $OSi(R^{26})_2$; $(CH_2)_n$; $(CH_2)_nNH$; $(CH_2)_nO$; optionally substituted $C_{1-16}$alkylaryl; optionally substituted aryl; optionally substituted polyaryl; optionally substituted $C_{3-6}$cycloaliphatic; and optionally substituted $C_{3-6}$heterocyclyl;

$R^{22}$ and $R^{23}$ are independently selected from the group consisting of H, OH, $NR^{11}R^{12}$, optionally substituted $C_{1-16}$alkyl, NCO, epoxy and $Si(R^{13})_3$;

$R^{24}$ and $R^{25}$ are independently selected from the group consisting of H and optionally substituted $C_{1-16}$alkyl;

$R^{26}$ is selected from the group consisting of optionally substituted $C_{1-16}$alkyl, $(CH_2)_nOH$ and $(CH_2)_nNH_2$;

n is 1 to 16;

p and r are independently selected from 1 to 1500;

q is 0 to 1500; and a reactive coating.

19. The polymer of claim 18, wherein the cross-linked reaction product further comprises at least one selected from the group consisting of a polyol, a polyamine, a polyisocyanate and a FPOSS polyisocyanate prepolymer of formula (I):

(I)

[chemical structure]

in which X is $(CH_2)_2OC(O)NH(CH_2)_2OC(O)CH(NCO)(CH_2)_4NCO$ or optionally substituted $C_{1-20}$ alkyl comprising at least two isocyanate groups, which may be optionally interrupted by O, $CH_2O$, Si, NH, $NR^{11}$, C=O, CH(OH), NH, CR(NCO), $(CH_2)_n$, or $CO_2$;

R is independently selected from a polyisocyanate, an optionally substituted $C_{1-20}$ alkyl, which may be optionally interrupted with O, C=O, N=C=O, CH(OH), $CH_2OR^{11}$, $CH_2SR^{11}$, or $(CH_2)_m(CF_2)_nCF_3$, provided that at least one R is $(CH_2)_m(CF_2)_nCF_3$;

m is 1 to 20;

n is 0 to 20; and $R^{11}$ is H or optionally substituted $C_{1-16}$ alkyl.

20. A polymer comprising a cross-linked reaction product of:
a FPOSS polyisocyanate prepolymer of formula (I) according to claim 1 and a reactive coating.

* * * * *

UNITED STATES PATENT AND TRADEMARK OFFICE
CERTIFICATE OF CORRECTION

PATENT NO. : 10,202,523 B2  
APPLICATION NO. : 15/313820  
DATED : February 12, 2019  
INVENTOR(S) : Berry et al.

Page 1 of 3

It is certified that error appears in the above-identified patent and that said Letters Patent is hereby corrected as shown below:

In the Specification

Column 2, Lines 40-53, replace Formula (I) with Formula (I) as follows:

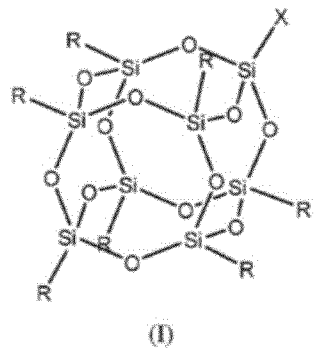

Column 8, Lines 33-48, replace Scheme 2 with the following Scheme 2:

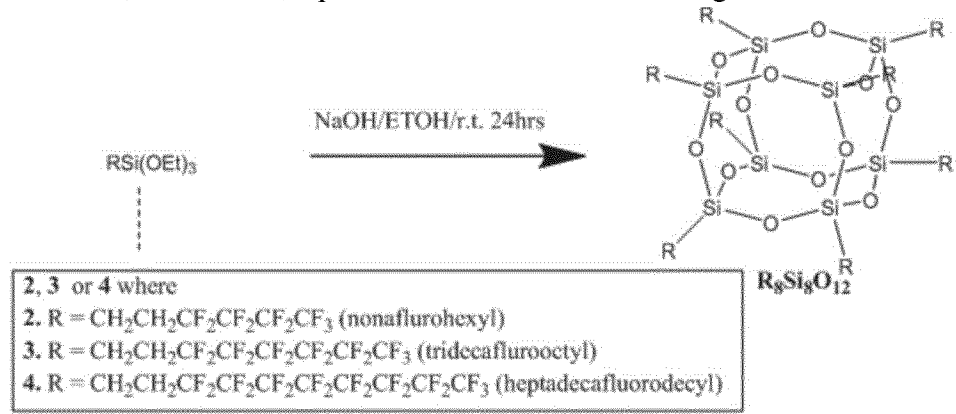

Signed and Sealed this  
Twenty-seventh Day of August, 2019

Andrei Iancu  
*Director of the United States Patent and Trademark Office*